(12) United States Patent
Brossaud et al.

(10) Patent No.: US 8,703,671 B2
(45) Date of Patent: Apr. 22, 2014

(54) PROCESS AND APPARATUS FOR PREPARING A UREA GREASE

(75) Inventors: Jean-luc Pierre André Brossaud, Petit Couronne (FR); David Edmund Code, Tomball, TX (US); Jerome Dabos, Petit Couronne (FR); Ronald David Harris, Katy, TX (US); Charles Montgomery Harris, Katy, TX (US); Aimin Huang, Sugar Land, TX (US); Krishna Rangraj Kaushik, Houston, TX (US); Catherine Maillard, Petit Couronne (FR); Howard Brian Mead, Ince Chester (GB); Raghunath Gopal Menon, Katy, TX (US); Jean-paul Saint, Petit Couronne (FR)

(73) Assignee: Shell Oil Company, Houston, TX (US)

( * ) Notice: Subject to any disclaimer, the term of this patent is extended or adjusted under 35 U.S.C. 154(b) by 974 days.

(21) Appl. No.: 12/517,733

(22) PCT Filed: Dec. 5, 2007

(86) PCT No.: PCT/US2007/086476
§ 371 (c)(1),
(2), (4) Date: Aug. 12, 2009

(87) PCT Pub. No.: WO2008/073773
PCT Pub. Date: Jun. 19, 2008

(65) Prior Publication Data
US 2010/0099592 A1    Apr. 22, 2010

Related U.S. Application Data

(60) Provisional application No. 60/869,058, filed on Dec. 7, 2006.

(51) Int. Cl.
| *C10M 115/08* | (2006.01) |
| *C10M 133/20* | (2006.01) |
| *C10M 149/20* | (2006.01) |
| *C07C 273/00* | (2006.01) |
| *C07C 275/00* | (2006.01) |

(52) U.S. Cl.
USPC ........... 508/386; 508/528; 508/552; 422/224; 564/61; 564/63

(58) Field of Classification Search
USPC .................. 508/552, 200, 386, 528; 422/224; 564/61, 63
See application file for complete search history.

(56) References Cited

U.S. PATENT DOCUMENTS 2,652,366 A * 9/1953 Wall et al. ...................... 508/519
4,104,177 A * 8/1978 Caruso .......................... 508/552
(Continued)

FOREIGN PATENT DOCUMENTS

EP    1626061    2/2006    ............... C08G 3/12
GB    1279127    6/1972    ............... C10M 5/14
(Continued)

*Primary Examiner* — Cephia D. Toomer
*Assistant Examiner* — Vishal Vasisth

(57) ABSTRACT

The invention provides for a process for preparing a urea grease including: (a) introducing a first feed component to a first feeding zone; (b) introducing a second feed component to a second feeding zone; (c) first reacting-mixing in a first reacting-mixing zone; and (d) cooling-mixing in a cooling-mixing zone. The invention also provides for a process for preparing a urea grease including: (a) introducing a first feed component to a first feeding zone; (b) introducing a second feed component to a second feeding zone; (c) first reacting-mixing in a first reacting-mixing zone; (d) introducing a third feed component to a third feeding zone; (e) second reacting-mixing in a second reacting-mixing zone; and (f) cooling-mixing in a cooling-mixing zone. The invention also provides for an apparatus for preparing a urea grease comprising: (a) a first feeding zone; (b) a second feeding zone; (c) a first reacting-mixing zone; and (d) a cooling-mixing zone. The invention also provides for an apparatus for preparing a urea grease comprising: (a) a first feeding zone; (b) a second feeding zone; (c) a first reacting-mixing zone; (d) a third feeding zone; (e) a second reacting-mixing zone; and (f) a cooling-mixing zone.

23 Claims, 3 Drawing Sheets

(56) References Cited

U.S. PATENT DOCUMENTS

| | | | |
|---|---|---|---|
| 4,392,967 A | | 7/1983 | Alexander ................... 252/41 |
| 5,314,982 A | * | 5/1994 | Rasp et al. .................... 528/48 |
| 5,554,586 A | * | 9/1996 | Pratt ............................. 508/552 |
| 6,136,762 A | * | 10/2000 | Yoshinari et al. ............. 508/552 |
| 2006/0058203 A1 | * | 3/2006 | Laufer et al. ................. 508/552 |
| 2007/0191238 A1 | * | 8/2007 | Fischer et al. ................ 508/465 |

FOREIGN PATENT DOCUMENTS

| WO | WO9703152 | 1/1997 | ........... C10M 141/10 |
|---|---|---|---|
| WO | WO2007143454 | 12/2007 | |

* cited by examiner

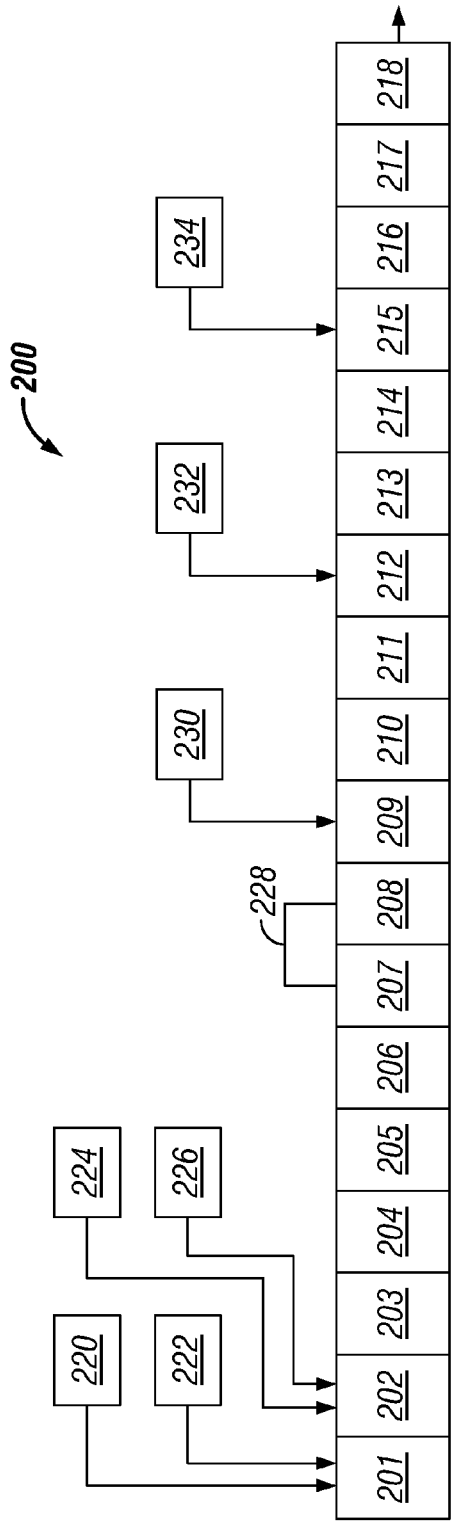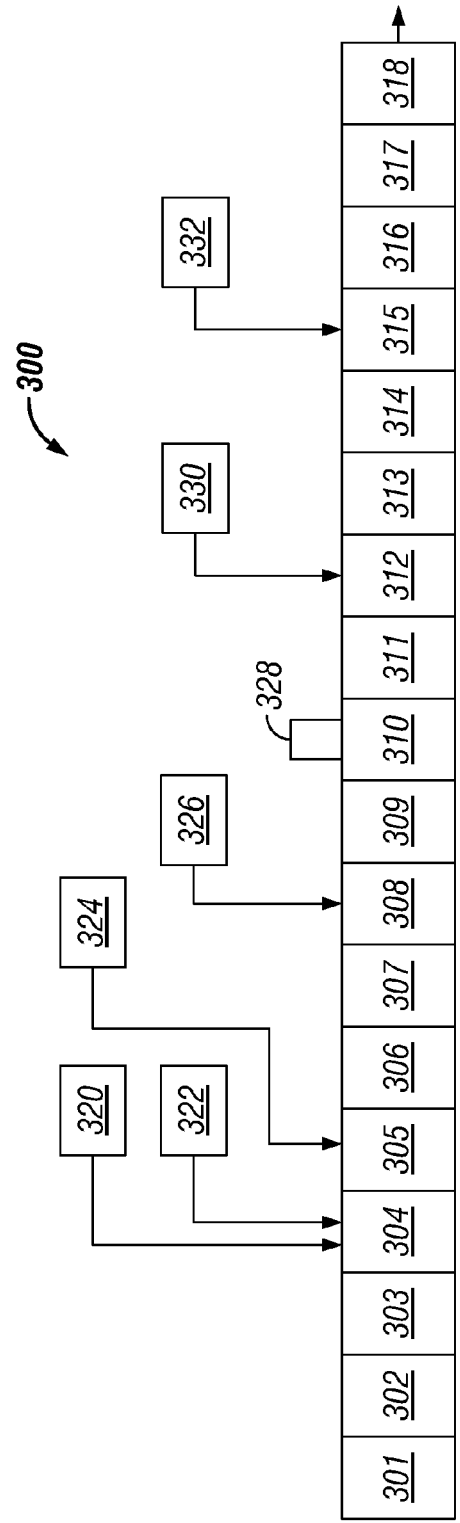

PROCESS AND APPARATUS FOR PREPARING A UREA GREASE

The present application claims priority from U.S. Provisional Patent Application 60/869,058 filed 7 Dec. 2006.

FIELD OF THE INVENTION

The invention relates to a process and an apparatus for preparing a urea grease.

BACKGROUND OF THE INVENTION

Urea grease has achieved rapid growth as a grease that may be conveniently applied to typical grease-lubricated applications including a wide variety of bearings for vehicle constant-velocity joints, ball joints, wheel bearings, alternators, cooling fans, ball screws, linear guides of machine tools, a wide variety of sliding areas of construction equipment, and bearings and gears in steel equipment and various other industrial mechanical facilities.

The usage of urea grease has been rising steadily in particular applications, such as various kinds of vehicle parts including constant-velocity joints (CVJs) where there is a strong demand for durability and reduced friction and wear in sliding areas in response to the trend of the present time toward miniaturization, weight reduction, and a hostile use environment, and in steel equipment that requires a highly heat-resistant, wear-resistant lubricating grease.

In addition to the individual components that make up a urea grease, another contributing factor to the final properties and characteristics of the urea grease is the particular process and conditions under which the urea grease is manufactured. Process conditions, for example, the dispersing and mixing of the individual components and temperature variations may be significant factors affecting the urea grease structure, for example, the nature of the fibers formed.

U.S. Pat. No. 5,314,982 to Christian Rasp et al. discloses a three-part process, which can also be employed on a large industrial scale, for the preparation of polyurea lubricating greases, which is characterised (a) in that polyureas which carry oleophilic groups are prepared by reaction of diisocyanates with amines either in the absence of a solvent on a reaction screw at 80°-120° C., preferably at 85°-95° C., (variant A) or in a toluene medium at 20°-80° C., preferably at 30°-60° C., (variant B), (b) in that, after complete reaction, the polyureas prepared according to (a) are ground in the solid, dry state to give powders (at least 70% by weight of the powder having particle sizes of about 100-400μ) and (c) in that the ground crude product, after being made into a "paste" (wetted) at elevated temperature in the base oil employed (10-30 minutes at 140°-180° C.) and cooled again to room temperature, is processed to a grease by complete homogenisation—if appropriate in several passes—in a high-pressure homogeniser under a pressure of 400-1,500 bar (spontaneous heating occurring up to 100° C.), greases having readily reproducible and essentially the same properties as in the case of the previously customary in situ manufacture being produced.

U.S. Pat. No. 4,392,967 to A. Gordon Alexander discloses a process for continuously manufacturing a lubricating grease using a screw process unit comprising: (a) introducing feed materials and lubricating oil into selected locations of a screw process unit which contains a series of adjacent, longitudinally connected barrel sections for performing different operative steps and houses a rotating screw device traversing the interior of the barrel sections and having separate elements along its length to perform desired operations; (b) mixing and conveying said feed materials along said process unit through the adjacent barrel sections by continuous operation of said rotating screw; (c) controlling the temperature of said material while it is being conveyed through said process unit by use of various heat exchange means which are located in or adjacent each barrel to aid in carrying out the operative steps of dispersion, reaction, dehydration and/or homogenization; (d) venting water resulting from the dehydration of the feed mixture at selected barrel discharge points in said process unit; (e) introduction of additional lubricating oil and/or additives at downstream barrel locations following the dehydration step; (f) homogenization of said complete grease formulation by continued rotation of said screw device; and (g) removal of the finished lubricating grease from the end barrel section of said screw process unit.

Despite the history of urea greases and processes of preparing urea greases, there is still a need for a continuous process of preparing a urea grease that will provide advantages regarding process, process stability, quality control, and economy. There is also still a need to provide for a process of preparing a urea grease that will provide for the flexibility to be applicable for many types of urea greases without significant changes in the equipment being used.

SUMMARY OF THE INVENTION

The invention provides for a process for preparing a urea grease comprising: (a) introducing a first feed component to a first feeding zone; (b) introducing a second feed component to a second feeding zone; (c) first reacting-mixing in a first reacting-mixing zone; and (d) cooling-mixing in a cooling-mixing zone.

The invention also provides for a process for preparing a urea grease comprising: (a) introducing a first feed component to a first feeding zone; (b) introducing a second feed component to a second feeding zone; (c) first reacting-mixing in a first reacting-mixing zone; (d) introducing a third feed component to a third feeding zone; (e) second reacting-mixing in a second reacting-mixing zone; and (f) cooling-mixing in a cooling-mixing zone.

The invention also provides for an apparatus for preparing a urea grease comprising: (a) a first feeding zone; (b) a second feeding zone; (c) a first reacting-mixing zone; and (d) a cooling-mixing zone.

The invention also provides for an apparatus for preparing a urea grease comprising: (a) a first feeding zone; (b) a second feeding zone; (c) a first reacting-mixing zone; (d) a third feeding zone; (e) a second reacting-mixing zone; and (f) a cooling-mixing zone.

BRIEF DESCRIPTION OF THE DRAWINGS

One or more embodiments of the invention are described in detail and by way of example only with reference to the accompanying drawings.

FIG. 3 schematically depicts an apparatus of the invention for preparing a tetraurea grease.

FIG. 4 schematically depicts an apparatus of the invention for preparing a diurea grease.

DETAILED DESCRIPTION OF THE INVENTION

Figure 1:
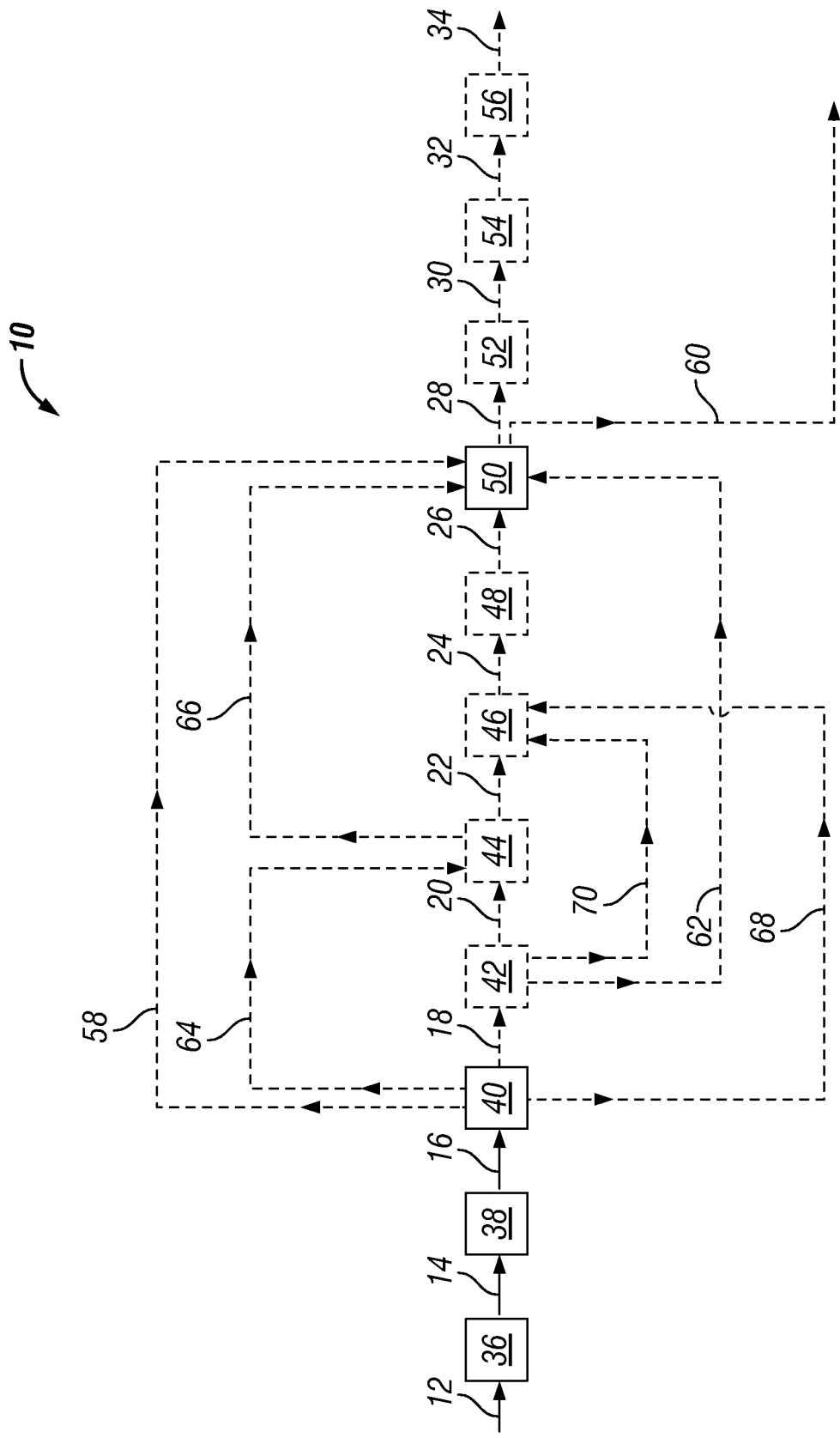
FIG. 1 schematically depicts a process for preparing a urea grease, for example, a tetraurea grease, according to a process of the invention.

The invention provides for a process for the preparation of a urea grease including, for example, a urea base grease, a urea finished grease, or a combination thereof. The invention preferably provides for a process for the continuous preparation of a urea grease including, for example, a urea base grease, a urea finished grease, or a combination thereof. As used herein, the terms "continuous" and "continuously" refer to a process of the invention being conducted generally uninterrupted in time and sequence compared to conventional techniques, for example, batch processing.

The invention provides for one or more of the following advantages.

An advantage of the invention is that a urea grease, for example, a diurea grease, or a triurea-urethane grease, or a tetraurea grease, or a combination thereof, may be continuously prepared utilizing a process of the invention.

Another advantage of the invention is the flexibility that is provided to adapt a process of the invention to provide for various types of urea grease, for example, a diurea grease, or a triurea-urethane grease, or a tetraurea grease, or a combination thereof, without the need for major changes in equipment or flow path.

A urea grease generally comprises a urea grease thickener and a base oil. A urea grease prepared or manufactured according to a process of the invention comprises a weight percent of urea grease thickener based on the total weight of urea grease generally in a range of from 2 weight percent to 25 weight percent, preferably in a range of from 3 weight percent to 20 weight percent, and more preferably in a range of from 5 weight percent to 20 weight percent.

Examples of a urea grease thickener include a diurea grease thickener, a triurea-urethane grease thickener, a tetraurea grease thickener, and combinations thereof. Also for example, cross-linking may occur when preparing urea grease thickeners.

A base oil, also referred to in the art as a lubricating oil, suitable for use in a process of the invention may typically be the same as a base oil that would normally be selected for oil lubrication or, for example, for preparing a grease from batch processing. The base oil, also referred to herein generally as an oil, may be of mineral origin, synthetic origin, or a combination thereof. Base oils of mineral origin may be mineral oils, for example, those produced by solvent refining or hydroprocessing. Base oils of synthetic origin may typically comprise mixtures of $C_{10}$-$C_{50}$ hydrocarbon polymers, for example, polymers of alpha-olefins, ester type synthetic oils, ether type synthetic oils, and combinations thereof. Base oils may also include Fischer-Tropsch derived highly paraffinic products.

Suitable examples of synthetic oils include polyolefins, for example, alpha-olefin oligomer and polybutene, polyalkylene glycols, for example, polyethylene glycol and polypropylene glycol, diesters, for example, di-2-ethyl hexyl sebacate and di-2-ethyl hexyl adipate, polyol esters, for example, trimethylolpropane ester and pentaerythritol ester, perfluoroalkyl ethers, silicone oils, polyphenyl ethers, either individually or as mixed oils.

Suitable examples of base oils include medium viscosity mineral oils, high viscosity mineral oils, and combinations thereof. Medium viscosity mineral oils have a viscosity generally in a range of from 5 $mm^2$/s centistokes (cSt) at 100° C. to 15 $mm^2$/s (cSt) at 100° C., preferably in a range of from 6 $mm^2$/s (cSt) at 100° C. to 12 $mm^2$/s (cSt) at 100° C., and more preferably in a range of from 7 $mm^2$/s (cSt) at 100° C. to 12 $mm^2$/s (cSt) at 100° C. High viscosity mineral oils have a viscosity generally in a range of from 15 $mm^2$/s (cSt) at 100° C. to 40 $mm^2$/s (cSt) at 100° C. and preferably in a range of from 15 $mm^2$/s (cSt) at 100° C. to 30 $mm^2$/s (cSt) at 100° C.

Suitable examples of mineral oils that may conveniently be used include those sold by member companies of the Shell Group under the designations "HVI", "MVIN", or "HMVIP". Polyalphaolefins and base oils of the type prepared by the hydroisomerisation of wax, for example, those sold by member companies of the Shell Group under the designation "XHVI" (trade mark), may also be used.

Examples of a suitable urea grease that may be prepared utilizing a process of the invention include a diurea grease, a triurea-urethane grease, a tetraurea grease, and combinations thereof.

An example tetraurea grease may be prepared utilizing a process of the invention by contacting a first feed component (A) having the formula OCN—R1-NCO, wherein R1 comprises a hydrocarbylene comprising from 2 to 30 carbon atoms, a second feed component (B) comprising a monoamine having the formula NH2R2, wherein R2 comprises a hydrocarbyl comprising from 2 to 30 carbon atoms, and another second feed component (C) comprising a diamine having the formula NH2R3NH2 wherein R3 comprises a hydrocarbylene comprising from 2 to 12 carbon atoms or a polyoxyhydrocarbylene comprising from 2 to 12 carbon atoms, in the presence of a base oil. The proportions by weight of the feed components comprising (A), (B), and (C) are determined by the stoichiometry of the chemical structure of the tetraurea grease thickener so that the feed components are fully reacted to provide the tetraurea grease thickener.

An example diurea grease may be prepared utilizing a process of the invention by contacting a first feed component (A) having the formula OCN—R1—NCO, wherein R1 comprises a hydrocarbylene comprising from 2 to 30 carbon atoms, and one or more of a feed component, for example, a feed component (D) and a feed component (E), comprising a monoamine having the formula NH2R2, wherein R2 comprises a hydrocarbyl comprising from 2 to 30 carbon atoms, in the presence of a base oil. The proportions by weight of the feed components comprising (A) and a monoamine, for example feed components (A), (D), and (E), are determined by the stoichiometry of the chemical structure of the diurea grease thickener so that the feed components are fully reacted to provide the diurea grease thickener.

A triurea-urethane grease may be prepared in a manner similar to preparing a diurea grease. A triurea-urethane grease generally comprises a triurea-monourethane molecule, and may also comprise a diurea molecule, a monourea-monourethane molecule, a diurethane molecule, or a combination thereof. An example triurea-urethane grease may be prepared utilizing a process of the invention by contacting a first feed component (A) having the formula OCN—R1—NCO, wherein R1 comprises a hydrocarbylene comprising from 2 to 30 carbon atoms, a feed component (F) comprising an alcohol, and a feed component comprising a monoamine having the formula NH2R2, wherein R2 comprises a hydrocarbyl comprising from 2 to 30 carbon atoms and a feed component comprising a diamine having the formula NH2R3NH2 wherein R3 comprises a hydrocarbylene comprising from 2 to 12 carbon atoms or a polyoxyhydrocarbylene comprising from 2 to 12 carbon atoms, in the presence of a base oil. Generally, the alcohol is reacted with the first feed component (A) before contacting with the amines. The feed component comprising a monoamine and the feed component comprising a diamine may comprise one feed component, for example, a feed component (G). The proportions by weight of the feed components comprising (A), an alcohol, a monoamine, and a diamine, for example, feed components (A), (F), and (G), are determined by the stoichiometry of the chemical structures of the triurea-urethane grease thickener so that the feed components are fully reacted to provide the triurea-urethane grease thickener.

The hydrocarbylene, as referred to herein in R1, comprises a divalent hydrocarbon radical that may be aliphatic, alicyclic, aromatic, or a combination thereof, for example, but not limited to, alkylarylene, aralkylene, alkylcycloalkylene, cycloalkylarylene, or a combination thereof, comprising two free valences on different carbon atoms. The hydrocarbyl, as referred to herein in R2, comprises a monovalent organic radical comprising hydrogen and carbon and may be aliphatic, aromatic, alicyclic, or a combination thereof, for example, but not limited to, aralkyl, alkyl, aryl, cycloalkyl, alkylcycloalkyl, or a combination thereof, and may be saturated or olefinically unsaturated (one or more double-bonded carbons, conjugated or non-conjugated).

The hydrocarbylene, as referred to herein in R3, comprises a divalent organic radical comprising hydrogen and carbon and may be aliphatic, aromatic, alicyclic, or a combination thereof, for example, but not limited to, aralkyl, alkyl, aryl, cycloalkyl, alkylcycloalkyl, or a combination thereof, and may be saturated or olefinically unsaturated (one or more double-bonded carbons, conjugated or non-conjugated). The polyoxyhydrocarbylene, as referred to herein in R3, comprises a divalent hydrocarbon radical that may be aliphatic, alicyclic, aromatic, or a combination thereof, for example, but not limited to, alkylarylene, aralkylene, alkylcycloalkylene, cycloalkylarylene, or a combination thereof, comprising two free valences on different carbon atoms, with repeating units from 2 to 5.

Examples of a suitable diisocyanate that may be utilized to prepare a urea grease utilizing a process of the invention include diphenylmethane diisocyanate, phenylene diisocyanate, diphenyl diisocyanate, phenyl diisocyanate, tolylene diisocyanate (TDI), naphthylene diisocyanate, tolylene ortho-diisocyanate (TODI), and combinations thereof. Examples of a suitable monoamine that may be utilized to prepare a urea grease utilizing a process of the invention include octylamine, dodecylamine (laurylamine), tetradecylamine (myristylamine), hexadecylamine, octadecylamine (tallow amine, also referred to as stearylamine), oleylamine, aniline, benzyl amine, p-toluidine, p-chloro-aniline, m-xylidine, and combinations thereof. Examples of a suitable diamine that may be utilized to prepare a urea grease utilizing a process of the invention include ethylenediamine (EDA), propylenediamine, butylenediamine, pentylenediamine, hexamethylenediamine (HMDA), polyoxymethylene diamine, polyoxyethylene diamine, polyoxypropylene diamine, polyoxyisopropylene diamine, polyetheramine, triethylene glycol diamine, and combinations thereof. Examples of a suitable alcohol that may be utilized to prepare a urea grease, for example a triurea-urethane grease, utilizing a process of the invention include 1-dodecanol (lauryl alcohol), 1-tetradecanol (myristyl alcohol), 1-hexadecanol (cetyl (or palmityl) alcohol), 1-octadecanol (stearyl alcohol), cis-9-octadecen-1-ol (oleyl alcohol), 9-octadecadien-1-ol (unsaturated palmitoleyl alcohol), 12-octadecadien-1-ol (linoleyl alcohol), and combinations thereof.

For example, a tetraurea grease may be prepared utilizing a process of the invention by contacting a first feed component (A) comprising, for example, tolylene diisocyanate (TDI) (for example, a blend of 20 weight percent tolylene 2,6-diisocyanate and 80 weight percent tolylene 2,4-diisocyanate), a second feed component (B) comprising, for example, 1-octadecylamine (also referred to as tallow amine), and another second feed component (C) comprising, for example, hexamethylenediamine (HMDA), in the presence of a base oil.

A weight ratio of second feed component (B) to another second feed component (C) may be any weight ratio that provides for the tetraurea grease. For example, a weight ratio of 1-octadecylamine to hexamethylenediamine (HMDA) may be in a range of from 4.2:1 to an upper limit that is limited by the minimum amount of hexamethylenediamine (HMDA) that is needed to provide for the tetraurea grease. An example upper limit may be 100:1 providing for an example weight ratio in a range of from 4.2:1 to 100:1. For example, 100 weight percent 1-octadecylamine and 0 weight percent hexamethylenediamine (HMDA) provides for a diurea grease with no tetraurea grease. In addition to the weight ratio of feed components (B) to (C), the remaining proportions of feed components comprising (A), (B), and (C) are determined by the stoichiometry of the chemical structure of the tetraurea grease thickener so that the feed components are fully reacted to provide the tetraurea grease thickener.

Also for example, a tetraurea grease may be prepared utilizing a process of the invention by contacting a first feed component (A) comprising, for example, tolylene diisocyanate (TDI) (for example, a blend of 20 weight percent tolylene 2,6-diisocyanate and 80 weight percent tolylene 2,4-diisocyanate), a second feed component (B) comprising, for example, 1-octadecylamine (also referred to as tallow amine), and another second feed component (C) comprising, for example, ethylenediamine (EDA), in the presence of a base oil.

A weight ratio of second feed component (B) to another second feed component (C) may be any weight ratio that provides for the tetraurea grease. For example, a weight ratio of 1-octadecylamine to ethylenediamine (EDA) may be in a range of from 8.1:1 to an upper limit that is limited by the minimum amount of ethylenediamine (EDA) that is needed to provide for the tetraurea grease. An example upper limit may be 100:1 providing for an example weight ratio in a range of from 8.1:1 to 100:1. For example, 100 weight percent 1-octadecylamine and 0 weight percent ethylenediamine (EDA) provides for a diurea grease with no tetraurea grease. In addition to the weight ratio of feed components (B) to (C), the remaining proportions of feed components comprising (A), (B), and (C) are determined by the stoichiometry of the chemical structure of the tetraurea grease thickener so that the feed components are fully reacted to provide the tetraurea grease thickener.

Also for example, a tetraurea grease may be prepared utilizing a process of the invention by contacting a first feed component (A) comprising, for example, 4,4'-diphenylmethane diisocyanate (also referred to as methylene diisocyanate or MDI), a second feed component (B) comprising, for example, 1-octadecylamine (also referred to as tallow amine), and another second feed component (C) comprising, for example, polyoxypropylene diamine (POD), in the presence of a base oil.

A weight ratio of second feed component (B) to another second feed component (C) may be any weight ratio that provides for the tetraurea grease. For example, a weight ratio of 1-octadecylamine to polyoxypropylene diamine (POD) may be in a range of from 2.3:1 to an upper limit that is limited by the minimum amount of polyoxypropylene diamine (POD) that is needed to provide for the tetraurea grease. An example upper limit may be 100:1 providing for an example weight ratio in a range of from 2.3:1 to 100:1. For example, 100 weight percent 1-octadecylamine and 0 weight percent polyoxypropylene diamine (POD) provides for a diurea grease with no tetraurea grease. In addition to the weight ratio of feed components (B) to (C), the remaining proportions of feed components comprising (A), (B), and (C) are determined by the stoichiometry of the chemical structure of the tetraurea grease thickener so that the feed components are fully reacted to provide the tetraurea grease thickener.

Also for example, a diurea grease may be prepared utilizing a process of the invention by contacting a first feed component (A) comprising, for example, 4,4'-diphenylmethane diisocyanate (also referred to as methylene diisocyanate or MDI), a second feed component (D) comprising, for example, octylamine, and a third feed component (E) comprising, for example, dodecylamine, in the presence of a base oil.

A weight ratio of second feed component (D) to third feed component (E) may be any weight ratio that provides for the diurea grease. For example, an amount of octylamine and dodecylamine may be in a range of from 100 weight percent octylamine and 0 weight percent dodecylamine to 0 weight percent octylamine and 100 weight percent dodecylamine. In addition to the amount of components (D) and (E), the remaining proportions of feed components comprising (A), (D), and (E) are determined by the stoichiometry of the chemical structure of the diurea grease thickener so that the feed components are fully reacted to provide the diurea grease thickener.

Also for example, a triurea-urethane grease may be prepared utilizing a process of the invention by contacting a first feed component (A) comprising, for example, tolylene diisocyanate (also referred to as TDI) (for example, a blend of 20 weight percent tolylene 2,6-diisocyanate and 80 weight percent tolylene 2,4-diisocyanate), a second feed component (F) comprising, for example, 1-octadecanol (stearyl alcohol), and a third feed component (G) comprising, for example, 1-octadecylamine (also referred to as tallow amine) and ethylenediamine (EDA), in the presence of a base oil.

Also for example, third feed component (G) may be separated into two feed components with one feed component comprising 1-octadecylamine and the other feed component comprising ethylenediamine. Generally, the amines may be added in any order. For example, to maximise the proportion of triurea-monourethane or tetraurea molecules, the diamine may generally be added before the monoamine. Also for example, when preparing a triurea-urethane grease, generally all the ethylenediamine (EDA) and part of the monoamine may be added in the presence of base oil as a third feed component and the balance of the monoamine may be added in the presence of base oil as a fourth feed component. Also for example, the order of the third feed component followed by the fourth feed component may be reversed in order to provide for a different thickener fibrous structure that may be advantageous for urea grease rolling bearing applications, gear applications, and combinations thereof.

A weight ratio of the components of feed component (G) may be any weight ratio that provides for the triurea-urethane grease. For example, a weight ratio of 1-octadecylamine to ethylenediamine (EDA) may be in a range of from 4.0:1 to 7.0:1 while maintaining the stoichiometry. A weight ratio of feed component (F) to feed component (G) may be any weight ratio that provides for the triurea-urethane grease. For example, a weight ratio of 1-octadecanol (stearyl alcohol) to ethylenediamine (EDA) may be in a range of from 4.5:1 to 6.0:1 while maintaining the stoichiometry. Also for example, when there is less ethylenediamine (EDA) than needed stoichiometrically, di-components may be made with individual diisocyanate molecules independent of the triurea-monourethane molecules. For example, if two monoamine molecules react with a diisocyanate molecule, then a diurea molecule is provided. Also for example, if a monoamine molecule and an alcohol molecule react with a diisocyanate molecule, then a monourea-monourethane molecule is provided. Also for example, if two alcohol molecules react with a diisocyanate molecule, then a diurethane molecule is provided. Thus, a urea grease comprising a triurea-monourethane molecule and a diurea molecule, a monourea-monourethane molecule, a diurethane molecule, or a combination thereof may be provided. In addition to the weight ratio of monoamine to diamine and the weight ratio of alcohol to diamine, the remaining proportions of the feed components are determined by the stoichiometry of the chemical structures of the triurea-urethane grease thickener so that the feed components are fully reacted to provide the triurea-urethane grease thickener.

A urea grease prepared according to a process of the invention may comprise one or more additives, in amounts normally used in this field of application, to impart certain desirable characteristics to the urea grease including, for example, oxidation stability, tackiness, extreme pressure properties, corrosion inhibition, reduced friction and wear, and combinations thereof.

Examples of suitable additives include antioxidants, antirust additives, anti-wear additives, extreme pressure additives, pour point depressants, metal deactivators, tackiness agents, viscosity index improvers, and combinations thereof.

Examples of suitable additives include extreme pressure/antiwear agents, for example, zinc salts, for example, zinc dialkyl or diaryl dithiophosphates, borates, molybdenum dithiophosphate, substituted thiadiazoles, polymeric nitrogen/phosphorus compounds made, for example, by reacting a dialkoxy amine with a substituted organic phosphate, amine phosphates, sulphurised sperm oils of natural or synthetic origin, sulphurised lard, sulphurised esters, sulphurised fatty acid esters, sulphurised materials, organophosphates, for example according to the formula $(OR)_3P=O$ where R is an alkyl, aryl or aralkyl group, and triphenyl phosphorothionate; one or more overbased metal-containing detergents, for example, calcium or magnesium alkyl salicylates, alkylarylsulphonates or alkylsulphonates; ashless dispersant additives, for example, reaction products of polyisobutenyl succinic anhydride and an amine or ester; antioxidants, for example, hindered phenols or amines, for example phenyl alpha naphthylamine; antirust additives, for example, zinc naphthenate; friction-modifying additives; viscosity-index improving agents; pour point depressing additives; tackiness agents, and combinations thereof. Solid materials, for example, graphite, finely divided molybdenum disulphide, talc, metal powders, and various polymers, for example, polyethylene wax may also be added to impart special properties. An example aryl group is a phenyl group. An example aralkyl is a benzyl group.

A urea grease prepared according to a process of the invention may comprise a single zinc dithiophosphate or a combination of two or more zinc dithiophosphates. Examples of suitable zinc dithiophosphates include zinc dialkyl dithiophosphates, zinc diaryl dithiophosphates, zinc alkylaryl dithiophosphates, and combinations thereof. A preferred zinc dithiophosphate is a zinc dialkyl dithiophosphate. The alkyl moieties of a zinc dialkyl dithiophosphate may be straight chain or branched chain and generally comprise from 1 carbon atom to 20 carbon atoms, preferably from 8 carbon atoms to 20 carbon atoms, and more preferably from 8 carbon atoms to 12 carbon atoms.

A urea grease prepared according to a process of the invention may comprise an additive comprising a single ashless dithiocarbamate or a combination of two or more ashless dithiocarbamates. Examples of suitable ashless dithiocarbamates include ashless dialkyl dithiocarbamates, diaryl dithiocarbamates, alkylaryl dithiocarbamates, and combinations thereof. A preferred ashless dithiocarbamate is an ashless dialkyldithiocarbamate, more preferably a methylene-bis-dialkyldithiocarbamate. The alkyl moieties of an ashless dialkyl dithiocarbamate may be straight or branched chain and preferably contain from 1 carbon atom to 12 carbon atoms, more preferably from 2 carbon atoms to 6 carbon atoms. An example of a preferred ashless dithiocarbamate is methylene-bis-dibutyl-dithiocarbamate.

A urea grease prepared according to a process of the invention may comprise from 0.1 weight percent to 15 weight percent, preferably from 0.1 weight percent to 5 weight percent, more preferably from 0.1 weight percent to 2 weight percent, and even more preferably from 0.2 weight percent to 1 weight percent of one or more additives based on the total weight of urea grease. For example, a combination of additives may be needed to achieve a higher weight percent of additive, for example 15 weight percent.

An embodiment of the invention generally comprises one or more zones. The zones may provide for a transporting of feed components, urea grease, or a combination thereof from one zone downstream to another zone. Transporting may be provided using any means that suitably provides for a process of the invention. Examples of suitable means for transporting include a screw element and a combination of screw elements.

Generally, when preparing a tetraurea grease, the zones include a first feeding zone, a second feeding zone, a first reacting-mixing zone, and a cooling-mixing zone. When preparing a tetraurea grease, the zones may further include a venting zone. When preparing a tetraurea grease, the zones may further include an oil-feeding zone. When preparing a tetraurea grease, the zones may further include a mixing zone.

Generally, when preparing a tetraurea grease, the zones are in the order as disclosed herein and may comprise combinations of the zones described herein. The tetraurea grease zones may comprise additional zones, for example, additional feeding zones, reacting-mixing zones, venting zones, oil-feeding zones, mixing zones, cooling-mixing zones, and combinations thereof.

An example profile of zones for preparing a tetraurea grease may include a first feeding zone, a second feeding zone, a first reacting-mixing zone, a venting zone, a first mixing zone, an oil-feeding zone, a second mixing zone, a second oil-feeding zone, a third mixing zone, a third oil-feeding zone, a fourth mixing zone, and a cooling-mixing zone.

Generally, when preparing a diurea grease, the zones include a first feeding zone, a second feeding zone, a first reacting-mixing zone, a third feeding zone, a second reacting-mixing zone, and a cooling-mixing zone.

Generally, when preparing a diurea grease, the zones are in the order as disclosed herein and may comprise combinations of the zones described herein. The diurea grease zones may comprise additional zones, for example, additional feeding zones, reacting-mixing zones, venting zones, oil-feeding zones, mixing zones, cooling-mixing zones, and combinations thereof.

An example profile of zones for preparing a diurea grease may include a first feeding zone, a second feeding zone, a first reacting-mixing zone, a third feeding zone, a second reacting-mixing zone, a venting zone, a first mixing zone, an oil-feeding zone, a second mixing zone, a second oil-feeding zone, a third mixing zone, and a cooling-mixing zone.

Generally, when preparing a triurea-urethane grease, the zones include a first feeding zone, a second feeding zone, a first reacting-mixing zone, a third feeding zone, a second reacting-mixing zone, and a cooling-mixing zone.

Generally, when preparing a triurea-urethane grease, the zones are in the order as disclosed herein and may comprise combinations of the zones described herein. The triurea-urethane grease zones may comprise additional zones, for example, additional feeding zones, reacting-mixing zones, venting zones, oil-feeding zones, mixing zones, cooling-mixing zones, and combinations thereof. For example, if third feed component (G) comprising a monoamine and a diamine are separated into two feed components, the additional zones may comprise a fourth feeding zone. Also for example, if third feed component (G) comprising a monoamine and a diamine are separated into two feed components, a reacting-mixing zone may be located between the third feeding zone and the fourth feeding zone.

An example profile of zones for preparing a triurea-urethane grease may include a first feeding zone, a second feeding zone, a first reacting-mixing zone, a third feeding zone, a second reacting-mixing zone, a venting zone, a first mixing zone, an oil-feeding zone, a second mixing zone, a second oil-feeding zone, a third mixing zone, and a cooling-mixing zone.

For example, there may be several iterations of an oil-feeding zone followed by a mixing zone. Depending on the grease consistency and cooling desired, there may be several iterations of oil-feeding in an oil-feeding zone followed by mixing in a mixing zone. For example, when preparing a tetraurea grease, there may be several iterations or sets, for example, three, of oil-feeding in an oil-feeding zone followed by mixing in a mixing zone. Also for example, when preparing a diurea grease, there may be several iterations or sets, for example, two, of oil-feeding in an oil-feeding zone followed by mixing in a mixing zone. Also for example, when preparing a triurea-urethane grease, there may be several iterations or sets, for example, two, of oil-feeding in an oil-feeding zone followed by mixing in a mixing zone.

Also for example, in addition to or in lieu of a base oil, one or more additives may be utilized to provide for a urea finished grease. For example, a urea base grease may be subjected to an iteration of oil-feeding in an oil-feeding zone followed by mixing in a mixing zone where, in addition to or in lieu of a base oil, one or more additives may be utilized to provide for an iteration of additive feeding in an oil-feeding zone (may be referred to as an additive-feeding zone) followed by mixing in a mixing zone (may be referred to as an additive-mixing zone) to provide for a urea finished grease. Also for example, the oil-feeding zone (additive-feeding zone) and the mixing zone (additive-mixing zone) may be combined as one zone for oil-feeding, additive-feeding, or a combination thereof, and mixing.

An apparatus for preparing a urea grease may further comprise urea grease processing apparatus comprising a static mixer(s), a homogenizer(s), a screen pack(s), or a combination thereof.

For example, the zones may provide for a urea base grease. The urea base grease may then be provided to urea grease processing apparatus including static mixers, homogenizers, screen packs, or a combination thereof, to provide for a urea finished grease. When the zones comprise a screw element, for example, an extruder, utilizing the additional urea grease processing apparatus may provide for the ability to use an extruder that is shorter than when an extruder is utilized to provide for a urea finished grease. Use of a short extruder followed by additional urea grease processing apparatus to provide for a urea finished grease may be more economical than use of a longer extruder without additional urea grease processing apparatus to provide for a urea finished grease.

The additional processing of a urea grease, for example, a urea base grease, utilizing additional urea grease processing apparatus may comprise using any static mixers, homogenizers, screen packs, or combinations thereof utilized in the preparing of a urea grease, for example, a urea finished grease. Screen packs may be used to homogenize, filter, or a combination thereof. Example screen packs may use single screen or multiple screens comprising various mesh sizes. Homogenization may be achieved by forcing, for example, squeezing, the urea grease through the screen pack.

For example, one or more additives may be added to the cooling-mixing zone in lieu of using urea grease processing apparatus to provide for a urea finished grease. Also for example, one or more additives may be added after the cooling-mixing zone, in other words, outside the cooling-mixing zone using, for example, urea grease processing apparatus, to provide for a urea finished grease. Also for example, a combination of adding one or more additives to the cooling-mixing zone and using urea grease processing apparatus may be utilized.

Also for example, instead of utilizing urea grease processing apparatus, additional zones may be utilized comprising an additive-feeding zone followed by an additive-mixing zone, followed by a second cooling-mixing zone.

For example, a process of the invention may be utilized to provide for a urea grease. The urea grease may be utilized as a feed component in a feeding zone of the invention to provide for a urea grease comprising two or more urea greases. Also for example, the urea grease may be utilized, in addition to or in lieu of a base oil, in an oil-feeding zone of the invention to provide for a urea grease comprising two or more urea greases. Also for example, the urea grease may be utilized, in addition to or in lieu of an additive, in an additive-feeding zone of the invention to provide for a urea grease comprising two or more urea greases.

For example, a diurea grease may be added to a process of the invention for preparing a urea grease, for example, a diurea grease, a triurea-urethane grease, a tetraurea grease, or a combination thereof to provide for a urea grease comprising the diurea grease and a diurea grease, a triurea-urethane grease, a tetraurea grease, or a combination thereof. Also for example, a triurea-urethane grease may be added to a process of the invention for preparing a urea grease, for example, a diurea grease, a triurea-urethane grease, a tetraurea grease, or a combination thereof to provide for a urea grease comprising the triurea-urethane grease and a diurea grease, a triurea-urethane grease, a tetraurea grease, or a combination thereof. Also for example, a tetraurea grease may be added to a process of the invention for preparing a urea grease, for example, a diurea grease, a triurea-urethane grease, a tetraurea grease, or a combination thereof to provide for a urea grease comprising the tetraurea grease and a diurea grease, a triurea-urethane grease, a tetraurea grease, or a combination thereof. Also for example, the urea grease, for example, the diurea grease, or the triurea-urethane grease, or the tetraurea grease, or a combination thereof that may be added to a process of the invention may be provided from a process of the invention, from another source, for example, from batch processing, or a combination thereof.

As can be seen from the numerous examples, a process of the invention may be utilized to provide for a variety of urea greases without significant changes in process and apparatus. Also for example, by utilizing the various zones of a process of the invention, it may be possible to provide for a urea grease, for example, a diurea grease, a triurea-urethane grease, a tetraurea grease, or a combination thereof, separately, or simultaneously, or a combination thereof. For example, by adjusting the various features of a process of the invention, a urea grease having desired qualities relating to, for example, mechanical stability, high temperature properties, lubricity, and combinations thereof, may be prepared.

The feeding zones, for example, the first feeding zone, the second feeding zone, and when present, the third feeding zone, suitably provide for the introducing of components. It may not be necessary to have or utilize the third feeding zone. For example, when preparing a tetraurea grease, second feed components (B) and (C) may be provided to the second feeding zone and the third feeding zone may not be present, or may be present and not utilized, or may be present and utilized as a mixing zone.

Also for example, when preparing a diurea grease, second feed component (D) may be provided to the second feeding zone and third feed component (E) may be provided to the third feeding zone.

Also for example, when preparing a triurea-urethane grease, second feed component (F) may be provided to the second feeding zone and third feed component (G) may be provided to the third feeding zone.

Examples of a first feed component, to be introduced to the first feeding zone, include a feed component (A) as described herein having the formula OCN—R1—NCO, wherein R1 comprises a hydrocarbylene comprising from 2 to 30 carbon atoms, for example 4,4'-diphenylmethane diisocyanate (also referred to as methylene diisocyanate or MDI) or tolylene diisocyanate (TDI) (for example, a blend of 20 weight percent tolylene 2,6-diisocyanate and 80 weight percent tolylene 2,4-diisocyanate). Feed component (A) may be in any suitable shape and form that provides for a process of the invention. Examples of a suitable state of feed component (A) include flakes, powder, and liquid. Flakes may be a preferred form of feed component (A) for reasons of health, safety, environmental, or a combination thereof.

Preferably, first feed component (A) is provided to the first feeding zone in the presence of a base oil. For example, a base oil may be included as a first feed component.

Introducing component (A) to the first feeding zone may provide for a melting of component (A) before component (A), for example, a molten component (A), is contacted with other components, for example, second feed components (B) and (C) as described herein when preparing a tetraurea grease, or a second feed component (D) and a third feed component (E) as described herein when preparing a diurea grease, or a second feed component (F) and a third feed component (G) as described herein when preparing a triurea-urethane grease. It has been discovered that better control of the reaction(s) of the invention may be obtained when the ingredients used are in the molten phase, liquid phase, or a combination thereof.

For example, when preparing a tetraurea grease, components to be provided to a second feeding zone may include a second feed component (B) as described herein comprising a monoamine having the formula NH2R2, wherein R2 comprises a hydrocarbyl comprising from 2 to 30 carbon atoms, and another second feed component (C) as described herein comprising a diamine having the formula NH2R3NH2 wherein R3 comprises a hydrocarbylene comprising from 2 to 12 carbon atoms or a polyoxyhydrocarbylene comprising from 2 to 12 carbon atoms. Preferably, second feed component (B) and second feed component (C) are added or injected to the second feeding zone as a blend. Preferably, second feed components (B) and (C) are provided to the second feeding zone in the presence of a base oil. For example, a base oil may be included as a second feed component.

For example, when preparing a diurea grease, components to be provided to a second feeding zone may include a second feed component (D) as described herein comprising a monoamine having the formula NH2R2, wherein R2 comprises a hydrocarbyl comprising from 2 to 30 carbon atoms, and components to be provided to a third feeding zone may include a third feed component (E) as described herein comprising a monoamine having the formula NH2R2, wherein R2 comprises a hydrocarbyl comprising from 2 to 30 carbon atoms. For example, second feed component (D) is provided to second feeding zone in the presence of a base oil and third feed component (E) is provided to the third feeding zone in the presence of a base oil. For example, a base oil may be included as a second feed component and as a third feed component.

It has been discovered that when preparing a diurea grease utilizing a process of the invention, separating or splitting the feeding points of a second feed component (D) and a third feed component (E) may provide for an improvement in the selectivity of the reaction than when a second feed component (D) and a third feed component (E) are added at the same feeding point.

For example, when preparing a triurea-urethane grease, components to be provided to a second feeding zone may include a second feed component (F) as described herein comprising an alcohol, for example, 1-octadecanol (stearyl alcohol), and components to be provided to a third feeding zone may include a third feed component (G) as described herein comprising a monoamine having the formula NH2R2, wherein R2 comprises a hydrocarbyl comprising from 2 to 30 carbon atoms, for example, 1-octadecylamine (also referred to as tallow amine), and a diamine having the formula NH2R3NH2 wherein R3 comprises a hydrocarbylene comprising from 2 to 12 carbon atoms or a polyoxyhydrocarbylene comprising from 2 to 12 carbon atoms, for example, ethylenediamine (EDA), in the presence of a base oil. Also for example, the third feed component (G) may be separated into a third feed component and a fourth feed component as described herein.

Also for example, second feed component (F) may be provided to second feeding zone in the presence of a base oil and third feed component (G) may be provided to the third feeding zone in the presence of a base oil. For example, a base oil may be included as a second feed component and as a third feed component.

Introducing components to the feeding zones may be provided by any means that suitably provides for a process of the invention. Examples of suitable means for introducing components to the feeding zones include pumps (for example, when utilizing liquid feed components), gravimetric feeders, volumetric feeders, and combinations thereof. An example of a suitable commercial pump includes a Cipex gear pump from Maag Pump Systems Textron A.G., Zurich, Switzerland. Examples of suitable commercial gravimetric feeders include K-Tron gravimetric feeders from K-Tron International, Inc., Pitman, N.J., USA, and Brabender gravimetric feeders from Brabender Technologie KG, Duisburg, Germany. When utilizing solid feed components, the solid feed components may be introduced to a feed hopper that may be fitted with a feed auger.

The pressure in the various zones may be any suitable pressure that provides for a process of the invention. The pressure in the various zones may generally be the result of the throughput, screw element, or a combination thereof.

The temperature of the first feeding zone may be any suitable temperature that provides for a feeding of a first feed component. The temperature of the first feeding zone is generally in a range of from 40° C. to 100° C., preferably in a range of from 50° C. to 90° C., and more preferably in a range of from 60° C. to 80° C.

When preparing a tetraurea grease, the temperature of the second feeding zone may be any suitable temperature that provides for the feeding of a second feed component. The temperature of the second feeding zone when preparing a tetraurea grease is generally in a range of from 50° C. to 110° C., preferably in a range of from 60° C. to 100° C., and more preferably in a range of from 70° C. to 90° C.

When preparing a diurea grease, the temperature of the second feeding zone may be any suitable temperature that provides for the feeding of a second feed component. The temperature of the second feeding zone when preparing a diurea grease is generally in a range of from 50° C. to 110° C., preferably in a range of from 60° C. to 100° C., and more preferably in a range of from 70° C. to 90° C.

When preparing a diurea grease, the temperature of the third feeding zone may be any suitable temperature that provides for the feeding of a third feed component. The temperature of the third feeding zone when preparing a diurea grease is generally in a range of from 120° C. to 180° C., preferably in a range of from 130° C. to 170° C., and more preferably in a range of from 140° C. to 160° C.

When preparing a triurea-urethane grease, the temperature of the second feeding zone may be any suitable temperature that provides for the feeding of a second feed component. The temperature of the second feeding zone when preparing a triurea-urethane grease is generally in a range of from 20° C. to 110° C., preferably in a range of from 60° C. to 100° C., and more preferably in a range of from 70° C. to 90° C.

When preparing a triurea-urethane grease, the temperature of the third feeding zone may be any suitable temperature that provides for the feeding of a third feed component. The temperature of the third feeding zone when preparing a triurea-urethane grease is generally in a range of from 50° C. to 130° C., preferably in a range of from 60° C. to 100° C., and more preferably in a range of from 65° C. to 80° C.

The feeding zones provide for a feeding of components. The feeding zones, for example, the first feeding zone, the second feeding zone, and, when present, the third feeding zone, may comprise, for example, a screw element or a combination of screw elements. The section of the screw element in the first feeding zone, the second feeding zone, and, when present, the third feeding zone, may include, for example, small pitch conveying elements, large pitch conveying elements, and combinations thereof. The conveying elements in the first feeding zone, the second feeding zone, and, when present, the third feeding zone, may depend on factors including, for example, the size of the apparatus, the diameter of the screw element, and combinations thereof. Examples of elements in the first feeding zone, the second feeding zone, and, when present, the third feeding zone, include 28/14, 28/28, 42/21, 42/42, 25/25, 40/40, 40/60, 60/30, and 60/60. The first number of the element indicates the pitch and the second number of the element indicates the length. For example, conveying element 28/14 indicates an element having a pitch of 28 millimeters (mm) and a length of 14 mm.

The first reacting-mixing zone suitably provides for a first reacting-mixing of components. Reacting-mixing in the first reacting-mixing zone (referred to herein as first reacting-mixing) provides for a reacting and mixing of feed components. For example, when preparing a tetraurea grease, first reacting-mixing in the first reacting-mixing zone provides for a reacting and mixing of first feed component (A), second feed component (B), and second feed component (C). Also for example, when preparing a diurea grease, first reacting-mixing in the first reacting-mixing zone provides for a reacting and mixing of first feed component (A) and second feed component (D). Also for example, when preparing a triurea-urethane grease, first reacting-mixing in the first reacting-mixing zone provides for a reacting and mixing of first feed component (A) and second feed component (F). The reacting and mixing in the first reacting-mixing zone may occur simultaneously, separately, or a combination thereof. For example, there may be a simultaneous reacting and mixing of feed components. Also for example, there may be a reacting of feed components followed by a mixing of the resulting composition provided by the reacting of the feed components. First reacting-mixing in the first reacting-mixing zone may provide for a shearing of the resulting composition.

First reacting-mixing in the first reacting-mixing zone may be provided using any means that suitably provides for a process of the invention. Examples of suitable means for first reacting-mixing in the first reacting-mixing zone include a screw element and a combination of screw elements.

The temperature of the first reacting-mixing zone may be any suitable temperature that provides for a reacting-mixing of components. The temperature of the first reacting-mixing zone is generally in a range of from 50° C. to 200° C., preferably in a range of from 70° C. to 190° C., and more preferably in a range of from 80° C. to 180° C.

When a second reacting-mixing zone is present, for example, when preparing a diurea grease or a triurea-urethane grease, the second reacting-mixing zone suitably provides for a reacting-mixing of components. Reacting-mixing in the second reacting-mixing zone (referred to herein as second reacting-mixing) provides for a reacting and mixing of feed components. For example, when preparing a diurea grease, second reacting-mixing in the second reacting-mixing zone may provide for a reacting and mixing of first feed component (A), second feed component (D), and third feed component (E). For example, when preparing a triurea-urethane grease, second reacting-mixing in the second reacting-mixing zone may provide for a reacting and mixing of first feed component (A), second feed component (F), and third feed component (G). Second reacting-mixing in the second reacting-mixing zone may provide for a shearing of the resulting composition. The reacting and mixing in the second reacting-mixing zone may occur simultaneously, separately, or a combination thereof. For example, there may be a simultaneous reacting and mixing of components. Also for example, there may be a reacting of components followed by a mixing of the resulting composition provided by the reacting of the components. Second reacting-mixing in the second reacting-mixing zone may provide for a shearing of the resulting composition Also for example, the third feeding zone and the second reacting-mixing zone utilized when preparing a diurea grease or a triurea-urethane grease may not be present when preparing a tetraurea grease, or may be present and not utilized, or may be present and utilized as one or more mixing zones when preparing a tetraurea grease.

Second reacting-mixing in the second reacting-mixing zone may be provided using any means that suitably provides for a process of the invention. Examples of suitable means for second reacting-mixing in the second reacting-mixing zone include a screw element and a combination of screw elements.

The temperature of the second reacting-mixing zone may be any suitable temperature that provides for a second reacting-mixing of components. The temperature of the second reacting-mixing zone is generally in a range of from 110° C. to 200° C., preferably in a range of from 150° C. to 200° C., and more preferably in a range of from 170° C. to 190° C.

The section of the screw element in the first reacting-mixing zone, and when present, second reacting-mixing zone, may include, for example, small pitch conveying elements, large pitch conveying elements, normal kneading elements, reverse kneading elements, mixing elements, under-cut conveying elements, spacers, and combinations thereof. The elements, spacers, and combinations thereof in the first reacting-mixing zone and second reacting-mixing zone may depend on factors including, for example, the size of the apparatus, the diameter of the screw element, and combinations thereof. Examples of conveying elements in the first reacting-mixing zone and second reacting-mixing zone include 28/14, 28/28, 42/21, 42/42, 25/25, 40/40, 40/60, 60/30, and 60/60. Examples of kneading elements in the first reacting-mixing zone and second reacting-mixing zone include KB 45/5/14, KB 45/5/14 Li, KB 45/5/20, KB 45/5/28, KB 45/5/20 Li, and KB 45/5/40. Examples of mixing elements in the first reacting-mixing zone and second reacting-mixing zone include ZME 6.5/13, TME/60, and SME 42/42. Examples of under-cut conveying elements in the first reacting-mixing zone and second reacting-mixing zone include 42/21SK and 42/42SK. When an element is described with three numbers, the first number indicates the staggering angle (degrees), the second number indicates the number of disks, and the third number indicates the length. KB indicates kneading blocks, ZME indicates teeth mixing element, TME indicates turbine mixing element, and SME indicates screw mixing element. When under-cut conveying elements are utilized, transition elements, for example, 42/21SKN, may be utilized to smoothly transition the root of the under-cut element to the standard self-wiped element profiles.

The cooling-mixing zones, for example, the cooling-mixing zone, and when present, second cooling-mixing zone, of a process of the invention, may provide for a cooling of the composition, preferably for a cooling and mixing of the composition. Cooling-mixing in the cooling-mixing zone (also referred to herein as first cooling-mixing) may provide for a cooled composition and may further provide for a transporting of the cooled composition to a location in the process where a composition, for example, a urea base grease may be obtained. When present, cooling-mixing in the second cooling-mixing zone (also referred to herein as second cooling-mixing) may provide for a cooled composition and may further provide for a transporting of the cooled composition to a location in the process where a composition, for example, a urea finished grease may be obtained. One or more additives may be provided to the cooling-mixing zone or after the cooling-mixing zone, in other words, outside the cooling-mixing zone using, for example, urea grease processing apparatus, to provide for a urea finished grease. Also, for example, an additive-feeding zone (for example, by using an oil-feeding zone to add one or more additives) followed by an additive-mixing zone (for example, by using a mixing zone) followed by a second cooling-mixing zone may be utilized in lieu of urea grease processing apparatus to provide for a urea finished grease.

When cooling-mixing in the cooling-mixing zone and, when present, second cooling-mixing in the second cooling-mixing zone, further provides for transporting, the transporting may be provided using any means that suitably provides for a process of the invention. Examples of suitable means for transporting in the cooling-mixing zone and, when present, second cooling-mixing zone, include a screw element and a combination of screw elements. Cooling-mixing in the first cooling-mixing zone and, when present, second cooling-mixing in the second cooling-mixing zone, may provide for a shearing of the resulting composition. The cooling and mixing in the first cooling-mixing zone may occur simultaneously, separately, or a combination thereof. When present, the cooling and mixing in the second cooling-mixing zone may occur simultaneously, separately, or a combination thereof.

The temperature of the cooling-mixing zone may be any suitable temperature that provides for a cooling-mixing. The temperature of the cooling-mixing zone is generally in a range of from 30° C. to 120° C., preferably in a range of from 40° C. to 110° C., and more preferably in a range of from 50° C. to 100° C.

When present, the temperature of the second cooling-mixing zone may be any suitable temperature that provides for a second cooling-mixing. The temperature of the second cooling-mixing zone is generally in a range of from 30° C. to 110° C., preferably in a range of from 40° C. to 100° C., and more preferably in a range of from 50° C. to 90° C.

The section of the screw element in the cooling-mixing zone, and when present, second cooling-mixing zone, may include, for example, small pitch conveying elements, large pitch conveying elements, normal kneading elements, reverse kneading elements, mixing elements, under-cut conveying elements, spacers, and combinations thereof. The elements, spacers, and combinations thereof in the cooling-mixing zone and second cooling-mixing zone may depend on factors including, for example, the size of the apparatus, the diameter of the screw element, and combinations thereof. Examples of conveying elements in the cooling-mixing zone and second cooling-mixing zone include 28/14, 28/28, 42/21, 42/42, 25/25, 40/40, 40/60, 60/30, and 60/60. Examples of kneading elements in the cooling-mixing zone and second cooling-mixing zone include KB 45/5/14, KB 45/5/14 Li, KB 45/5/20, KB 45/5/28, KB 45/5/20 Li, and KB 45/5/40. Examples of mixing elements in the cooling-mixing zone and second cooling-mixing zone include ZME 6.5/13, TME/60, and SME 42/42. Examples of under-cut conveying elements in the cooling-mixing zone and second cooling-mixing zone include 42/21SK and 42/42SK. When under-cut conveying elements are utilized, transition elements, for example, 42/21SKN, may be utilized to smoothly transition the root of the under-cut element to the standard self-wiped element profiles.

Also for example, a process of the invention may further comprise deaerating the urea grease. For example, a cooling-mixing zone, and when present, a second cooling-mixing zone, or a combination thereof may comprise deaerating apparatus to provide for a deaerated urea base grease, a deaerated urea finished grease, or a combination thereof. Any deaerating apparatus that may provide for a removing of air, gas, or a combination thereof, from a urea grease may be utilized.

Also for example, if a resulting urea grease is at a temperature and composition where no further cooling, mixing, or a combination thereof is desired, the cooling-mixing zone, and when present, second cooling-mixing zone, may be used to convey or transport the urea grease to a location where a urea grease may be obtained.

A venting zone is an option of a process of the invention. For example, when preparing a tetraurea grease, a venting zone may be present after the first reacting-mixing zone. Also for example, when preparing a diurea grease or a triureaurethane grease, a venting zone may be present after the second reacting-mixing zone. When a venting zone is utilized, venting in the venting zone may provide for a venting of components, for example, carbon dioxide, to provide for a vented composition. Carbon dioxide may be formed from water that may be present in the feed components. Venting in the venting zone may be provided using any means that suitably provides for a process of the invention. Examples of suitable means for venting in a venting zone include atmospheric vents, light vacuum vents, and combinations thereof. A preferred means for venting in a venting zone may comprise the use of light vacuum vents.

When a venting zone is present, the temperature of the venting zone may be any suitable temperature that provides for venting. The temperature of the venting zone is generally in a range of from 130° C. to 190° C., preferably in a range of from 140° C. to 190° C., and more preferably in a range of from 150° C. to 185° C.

The venting zone may comprise, for example, a screw element or a combination of screw elements. The section of the screw element in the venting zone may include, for example, small pitch conveying elements or large pitch conveying elements. The elements in the venting zone may depend on factors including, for example, the size of the apparatus, the diameter of the screw element, and combinations thereof. Examples of conveying elements in the venting zone include 28/14, 28/28, 42/21, 42/42, 25/25, 40/40, 40/60, 60/30, and 60/60.

A mixing zone is an option of a process of the invention. For example, when preparing a urea grease, a mixing zone may be present after, in other words, downstream of, a venting zone, an oil-feeding zone, an additive-feeding zone, or a combination thereof. If a venting zone is utilized in preparing a tetraurea grease, for example, when utilizing a venting zone downstream of a first reacting-mixing zone, a mixing zone may be utilized downstream of the venting zone. If a venting zone is utilized in preparing a diurea grease or a triureaurethane grease, for example, when utilizing a venting zone downstream of a second reacting-mixing zone, a mixing zone may be utilized downstream of the venting zone.

Examples of suitable means for mixing in the mixing zone include a screw element and a combination of screw elements. Mixing in the mixing zone may further provide for a cooling of the composition. Mixing in the mixing zone may also provide for a transporting of the composition, a cooling of the composition, or a combination thereof. Mixing in the mixing zone may provide for a shearing of the composition that may provide for fiber formation.

The section of the screw element in the mixing zone may include, for example, small pitch conveying elements, large pitch conveying elements, normal kneading elements, reverse kneading elements, mixing elements, under-cut conveying elements, spacers, and combinations thereof. The elements, spacers, and combinations thereof in the mixing zone may depend on factors including, for example, the size of the apparatus, the diameter of the screw element, and combinations thereof. Examples of conveying elements in the mixing zone include 28/14, 28/28, 42/21, 42/42, 25/25, 40/40, 40/60, 60/30, and 60/60. Examples of kneading elements in the mixing zone include KB 45/5/14, KB 45/5/14 Li, KB 45/5/20, KB 45/5/28, KB 45/5/20 Li, and KB 45/5/40. Examples of mixing elements in the mixing zone include ZME 6.5/13, TME/60, and SME 42/42. Examples of under-cut conveying elements in the mixing zone include 42/21SK and 42/42SK. When under-cut conveying elements are utilized, transition elements, for example, 42/21SKN, may be utilized to smoothly transition the root of the under-cut element to the standard self-wiped element profiles.

The temperature of the mixing zone may be any suitable temperature that provides for mixing. The temperature of the mixing zone is generally in a range of from 80° C. to 200° C., preferably in a range of from 90° C. to 190° C., and more preferably in a range of from 100° C. to 180° C.

An oil-feeding zone is an option of a process of the invention. For example, if a sufficient amount of base oil is provided to the feeding zones, for example, the first feeding zone, the second feeding zone, and when present, the third feeding zone, an oil-feeding zone may not be needed.

Also, for example, if additional urea grease processing apparatus, for example, homogenizers, static mixers, screen packs, and combinations thereof are utilized to provide for a urea finished grease, an oil-feeding zone (utilized as an additive-feeding zone) followed by a mixing zone followed by a second cooling-mixing zone may not be needed.

Introducing a base oil may be provided by any means that suitably provides for a process of the invention. Examples of suitable means for introducing a base oil to an oil-feeding zone include pumps. An example of a suitable commercial pump for oil-feeding includes a Cipex gear pump from Maag Pump Systems Textron A.G., Zurich, Switzerland.

When an oil-feeding zone is present, oil-feeding in the oil-feeding zone may further provide for a transporting of the composition to zones located after, in other words, downstream of, the oil-feeding zone. When oil-feeding in the oil-feeding zone further provides for transporting, the transporting may be provided using any means that suitably provides for a process of the invention. Examples of suitable means for transporting in the oil-feeding zone include a screw element and a combination of screw elements. Oil-feeding in the oil-feeding zone may further provide for a cooling of the composition. Oil-feeding in the oil-feeding zone may provide for both a transporting and cooling of the composition.

The section of the screw element in the oil-feeding zone may include, for example, small pitch conveying elements, large pitch conveying elements, normal kneading elements, reverse kneading elements, mixing elements, under-cut conveying elements, spacers, and combinations thereof. The conveying elements, spacers, and combinations thereof in the oil-feeding zone may depend on factors including, for example, the size of the apparatus, the diameter of the screw element, and combinations thereof. Examples of elements in the oil-feeding zone include 28/14, 28/28, 42/21, 42/42, 25/25, 40/40, 40/60, 60/30, and 60/60. Examples of kneading elements in the oil-feeding zone include KB 45/5/14, KB 45/5/14 Li, KB 45/5/20, KB 45/5/28, KB 45/5/20 Li, and KB 45/5/40. Examples of mixing elements in the oil-feeding zone include ZME 6.5/13, TME/60, and SME 42/42. Examples of under-cut conveying elements in the oil-feeding zone include 42/21SK and 42/42SK. When under-cut conveying elements are utilized, transition elements, for example, 42/21SKN, may be utilized to smoothly transition the root of the under-cut element to the standard self-wiped element profiles.

The temperature of the oil-feeding zone may be any suitable temperature that provides for the feeding of oil. The temperature of the oil-feeding zone is generally in a range of from 50° C. to 150° C., preferably in a range of from 60° C. to 140° C., and more preferably in a range of from 70° C. to 130° C. The temperature of the oil-feeding zone may be related to the location of the oil-feeding zone. For example, an oil-feeding zone located near the first reacting-mixing zone, or when present, the second reacting-mixing zone, may comprise a higher temperature than an oil-feeding zone located near the cooling-mixing zone.

When an oil-feeding zone is utilized, the oil-feeding zone may be followed by a mixing zone. In other words, a mixing zone may be downstream of an oil-feeding zone. A mixing zone downstream of an oil-feeding zone may provide for a mixing of the oil and the components or composition present in the oil-feeding zone. Depending on the amount of oil that may be added, there may be one or more iterations of an oil-feeding zone followed by a mixing zone. Also for example, the oil-feeding zone and the mixing zone may be combined as one zone for oil-feeding and mixing.

The temperature of the various zones described herein may be maintained by any suitable means for heat exchanging known in the art. Examples of suitable means for heat exchanging include electrical heaters, fuel heaters, ceramic heaters, calrod heaters, coil-type heaters, and combinations thereof. A preferred means for heat exchanging is an electrical heater.

For example, when the various zones comprise barrels, the means for heat exchanging may generally comprise a passage, for example, a channel, a chamber, a bore, and combinations thereof in the barrel for carrying selected heat transfer media. The means for heat exchanging may be an electrical heater, for example, a calrod or coil-type heater. The means for heat exchanging are generally circumferentially located in or adjacent each barrel around the bore or central opening which houses a screw element. Such means for heat exchanging, while preferably close to the central opening, may be placed around the exterior part of the individual barrels in a coil-like manner, for example, insulated electrical heaters. Means for heat exchanging may also be placed in or along the shaft of a screw element. A preferred type of means for heat exchanging is a passage carrying heat transfer media. Any fluid may be used as the heat transfer media, for example, water, petroleum oils, and combinations thereof, and selecting a heat transfer media will depend on the particular temperature desired and the ease of handling in a process of the invention. The means for heat exchanging may provide for heating, cooling, or a combination thereof.

The zones described herein may comprise any suitable structure that provides for a process of the invention. Examples of suitable structures include reactor vessels, a series of individual barrels, and combinations thereof. A preferred structure comprises a series of individual barrels. A more preferred structure comprises a series of individual barrels that are adjacent to one another and longitudinally connected to allow for the different operative steps to be sequentially performed. Generally, the series of individual barrels house a screw element or a combination of screw elements that runs through the entire length of the series of individual barrels.

Examples of a suitable screw element include a single-screw element, a twin-screw element in a counter-rotating configuration, and a twin-screw element in a co-rotating configuration. Preferably, a screw element comprises a twin-screw element in a co-rotating configuration. Any commercial twin-screw co-rotating extruder that may provide for a process of the invention may be utilized. Also, any commercial twin-rotor continuous mixer that may provide for a process of the invention may be utilized.

An embodiment of a process of the invention may comprise utilizing an extruder. An embodiment of an apparatus of the invention may comprise an extruder.

Examples of a suitable commercial twin-screw co-rotating extruder for preparing a urea grease according to a process of the invention include a 40-mm twin-screw co-rotating extruder from Coperion Werner and Pfleiderer, Stuttgart, Germany, having model number ZSK40MC, a 34-mm, Mega Volume twin-screw co-rotating extruder from Coperion Werner and Pfleiderer, Stuttgart, Germany, having model number ZSK34MV, a 62-mm twin-screw co-rotating extruder from Coperion Werner and Pfleiderer, Stuttgart, Germany, having model number ZSK62, and a 125-mm twin-screw co-rotating extruder from Coperion Werner and Pfleiderer, Stuttgart, Germany, having model number ZSK125.

Examples of a suitable commercial continuous mixer include the FCM from Farell Corporation, Ansonia, Conn., USA and the CMP and CIM series from Japan Steel Works, Hiroshima, Japan.

A screw element of an embodiment of the invention may comprise various segments of different sizes, shapes, angles, and configurations as described herein that may help provide for the various processes to be conducted in the various zones. The screw element comprising various segments may provide for the various processes of the zones to be conducted along the length of the screw element by the selection of the various sizes, shapes, angles, and configurations of the screw element.

When a screw element is utilized, an apparatus of the invention further comprises a means for driving the screw element. The means for driving the screw element may be any suitable means that provides for a process of the invention. Examples of suitable means for driving the screw element include an electric motor and a fuel motor. A preferred means for driving the screw element is an electric motor.

When an apparatus of the invention comprises a screw element, the screw speed may be any speed that suitably provides for a process of the invention to provide for a urea grease. The screw speed is generally in a range of from 50 revolutions per minute (rpm) to 1200 rpm, preferably in a range of from 250 rpm to 700 rpm, and more preferably in a range of from 300 rpm to 600 rpm.

The total rate of throughput of components through an apparatus of the invention generally depends on factors including, for example, the quantity of urea grease that is to be produced, the size of the apparatus, the screw element diameter, and combinations thereof. For example, a small commercial twin-screw co-rotating extruder may provide for a low rate of throughput of components whereas a large commercial twin-screw co-rotating extruder may provide for a higher rate of throughput of components.

When an apparatus of the invention comprises a series of individual barrels that are adjacent to one another and longitudinally connected to allow for the different operative steps to be sequentially performed and housing a screw element that runs through the entire length of the series of individual barrels, the number of barrels may be any number that suitably provides for a process of the invention. The size and number of barrels generally depends on a variety of factors including, for example, the quantity of composition to be prepared, the rate of producing the composition, the size of the screw element, the number of process steps to be conducted, and combinations thereof.

The number of barrels utilized when preparing a urea grease according to a process of the invention is generally in a range of from 5 barrels to 25 barrels, preferably in a range of from 7 barrels to 20 barrels, and more preferably in a range of from 10 barrels to 18 barrels. A preferred apparatus of the invention for use in preparing a urea base grease comprises 15 barrels. A preferred apparatus of the invention for use in preparing a urea finished grease comprises 18 barrels. An apparatus for preparing a urea finished grease may comprise an additive-feeding zone (for example, an oil-feeding zone used to add one or more additives in addition to or in lieu of oil) followed by a mixing zone followed by a second cooling-mixing zone.

Storing and transporting a urea grease prepared according to a process of the invention may be conducted utilizing any temperature and technique used in the art of storing and transporting a urea grease. Examples of storing and transporting include the use of drums, pails, totes, and combinations thereof, generally with caustic resistant liners. Storage life may be increased by storing under an inert atmosphere, for example, nitrogen or argon.

FIG. 1 through FIG. 4 disclose one or more embodiments of the invention. For the sake of clarity, typical components utilized in preparing a urea grease, for example, pipes, valves, metering devices, pumps, controls, and combinations thereof have been generally omitted. While FIG. 1 through FIG. 4 may disclose flow(s) using one combined flow path, separate individual flow paths may be utilized.

Referring to FIG. 1, a series of zones 10 is disclosed for preparing a urea grease, for example, a tetraurea grease. The dotted lines indicate optional zones and flow paths that may be present and utilized, may be present and not utilized, or may not be present. A first feed component is introduced via 12 to first feeding zone 36. The first feed component from first feeding zone 36 passes via 14 to second feeding zone 38 where a second feed component is introduced. The resulting composition from second feeding zone 38 passes to first reacting-mixing zone 40 via 16 to provide for a first-reacted composition. The first-reacted composition from first reacting-mixing zone 40 passes to cooling-mixing zone 50 via 58 to provide for a cooled composition. A cooled composition is then obtained via 60. Optionally, the first-reacted composition may pass from first reacting-mixing zone 40 to venting zone 42 via 18 to provide for a vented composition. The vented composition may pass from venting zone 42 to cooling-mixing zone 50 via 62. A cooled composition may then be obtained via 60. Also optionally, the first-reacted composition may pass from first reacting-mixing zone 40 to first mixing zone 44 via 64. The resulting composition from first mixing zone 44 may pass to cooling-mixing zone 50 via 66. A cooled composition may then be obtained via 60. Also optionally, a first-reacted composition may pass from first reacting-mixing zone 40 to oil-feeding zone 46 via 68. The resulting composition from oil-feeding zone 46 may pass to second mixing zone 48 via 24. The resulting composition from second mixing zone 48 may pass to cooling-mixing zone 50 via 26. A cooled composition may then be obtained via 60. Also optionally, the first-reacted composition may pass from first reacting-mixing zone 40 to venting zone 42 via 18 to provide for a vented composition. The vented composition may pass from venting zone 42 to oil-feeding zone 46 via 70. The resulting composition from oil-feeding zone 46 may pass to second mixing zone 48 via 24. The resulting composition from second mixing zone 48 may pass to cooling-mixing zone 50 via 26. A cooled composition may then be obtained via 60. Also optionally, the first-reacted composition may pass from first reacting-mixing zone 40 to venting zone 42 via 18 to provide for a vented composition. The vented composition may pass from venting zone 42 to first mixing zone 44 via 20. The resulting composition from first mixing zone 44 may pass to oil-feeding zone 46 via 22. The resulting composition from oil-feeding zone 46 may pass to second mixing zone 48 via 24. The resulting composition from second mixing zone 48 may pass to cooling-mixing zone 50 via 26. A cooled composition may then be obtained via 60. Also for example, oil-feeding zone 46 and second mixing zone 48 may be combined as one zone where oil-feeding and mixing may occur.

Also optionally, in lieu of, or in addition to, obtaining a cooled composition from cooling-mixing zone 50 via 60, the cooled composition may pass from cooling-mixing zone 50 to second oil-feeding zone 52 via 28. When one or more additives are added, for example, to provide for a urea finished grease, second oil-feeding zone 52 may be referred to as additive-feeding zone 52. The resulting composition from second oil-feeding zone 52 may pass to third mixing zone 54 (may also be referred to as additive-mixing zone 54 when one or more additives are added) via 30. The resulting composition from third mixing zone 54 may pass to second cooling-mixing zone 56 via 32 to provide for a second-cooled composition. The second-cooled composition may then be obtained via 34. Also for example, second oil-feeding zone 52 and third mixing zone 54 may be combined as one zone where oil-feeding, additive-feeding, or a combination thereof, and mixing may occur.

Figure 2:
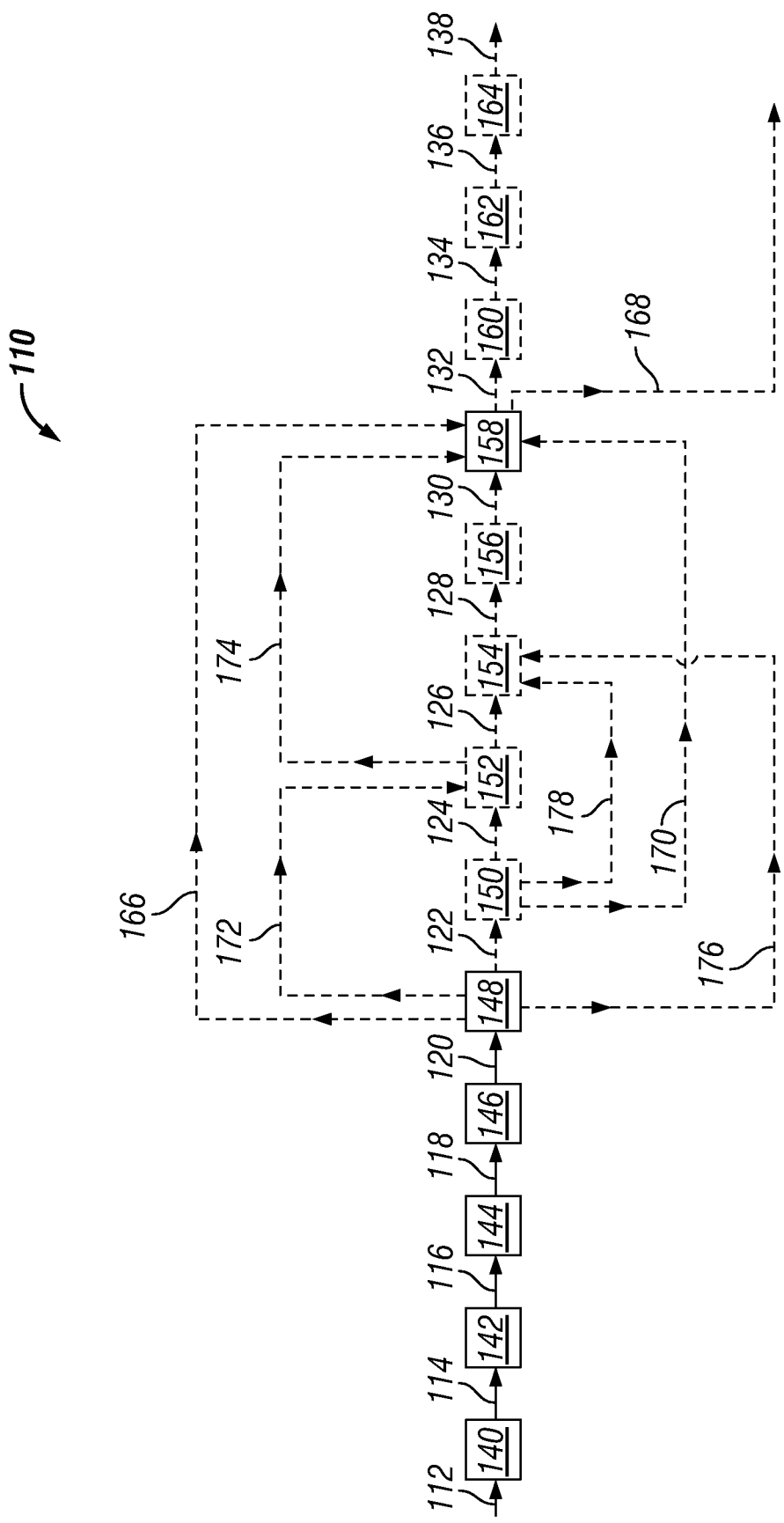
FIG. 2 schematically depicts a process for preparing a urea grease, for example, a diurea grease or a triurea-urethane grease, according to a process of the invention.

Referring to FIG. 2, a series of zones 110 is disclosed for preparing a urea grease, for example, a diurea grease or a triurea-urethane grease. The dotted lines indicate optional zones and flow paths that may be present and utilized, may be present and not utilized, or may not be present. A first feed component is introduced via 112 to first feeding zone 140. The first feed component from first feeding zone 140 passes via 114 to second feeding zone 142 where a second feed component is introduced. The resulting composition from second feeding zone 142 passes to first reacting-mixing zone 144 via 116 to provide for a first-reacted composition. The first-reacted composition from first reacting-mixing zone 144 passes via 118 to third feeding zone 146 where a third feed component is introduced. The resulting composition from third feeding zone 146 passes via 120 to second reacting-mixing zone 148 to provide for a second-reacted composition. The second-reacted composition passes to cooling-mixing zone 158 via 166 to provide for a cooled composition. A cooled composition is then obtained via 168.

Optionally, third feeding zone 146 may be separated into two feeding zones (not shown) generally comprising a third feeding zone and a fourth feeding zone. For example, when two feed components are introduced in third feeding zone 146, third feeding zone 146 may be separated into two feeding zones with a feed component being introduced in a third feeding zone and the other feed component being introduced in a fourth feeding zone. Also optionally, when third feeding zone 146 is separated into two feeding zones, a reacting-mixing zone (not shown) may be present between the two feeding zones.

Optionally, the second-reacted composition may pass from second reacting-mixing zone 148 to venting zone 150 via 122 to provide for a vented composition. The vented composition may pass from venting zone 150 to cooling-mixing zone 158 via 170. A cooled composition may then be obtained via 168. Also optionally, the second-reacted composition may pass from second reacting-mixing zone 148 to first mixing zone 152 via 172. The resulting composition from first mixing zone 152 may pass to cooling-mixing zone 158 via 174. A cooled composition may then be obtained via 168. Also optionally, a second-reacted composition may pass from second reacting-mixing zone 148 to oil-feeding zone 154 via 176. The resulting composition from oil-feeding zone 154 may pass to second mixing zone 156 via 128. The resulting composition from second mixing zone 156 may pass to cooling-mixing zone 158 via 130. A cooled composition may then be obtained via 168. Also optionally, the second-reacted composition may pass from second reacting-mixing zone 148 to venting zone 150 via 122 to provide for a vented composition. The vented composition may pass from venting zone 150 to oil-feeding zone 154 via 178. The resulting composition from oil-feeding zone 154 may pass to second mixing zone 156 via 128. The resulting composition from second mixing zone 156 may pass to cooling-mixing zone 158 via 130. A cooled composition may then be obtained via 168. Also optionally, the second-reacted composition may pass from second reacting-mixing zone 148 to venting zone 150 via 122 to provide for a vented composition. The vented composition may pass from venting zone 150 to first mixing zone 152 via 124. The resulting composition from first mixing zone 152 may pass to oil-feeding zone 154 via 126. The resulting composition from oil-feeding zone 154 may pass to second mixing zone 156 via 128. The resulting composition from second mixing zone 156 may pass to cooling-mixing zone 158 via 130. A cooled composition may then be obtained via 168. Also for example, oil-feeding zone 154 and second mixing zone 156 may be combined as one zone where oil-feeding and mixing may occur.

Also optionally, in lieu of, or in addition to, obtaining a cooled composition from cooling-mixing zone 158 via 168, the cooled composition may pass from cooling-mixing zone 158 to second oil-feeding zone 160 via 132. When one or more additives are added, for example, to provide for a urea finished grease, second oil-feeding zone 160 may be referred to as an additive-feeding zone 160. The resulting composition from second oil-feeding zone 160 may pass to third mixing zone 162 (may also be referred to as additive-mixing zone 162 when one or more additives are added) via 134. The resulting composition from third mixing zone 162 may pass to second cooling-mixing zone 164 via 136 to provide for a second-cooled composition. The second-cooled composition may then be obtained via 138. Also for example, second oil-feeding zone 160 and third mixing zone 162 may be combined as one zone where oil-feeding, additive-feeding, or a combination thereof, and mixing may occur.

Referring to FIG. 3, a schematic of an apparatus 200 is disclosed comprising a screw element, for example, a twin-screw co-rotating extruder, similar to the apparatus referred to herein in the EXAMPLES, to provide for a urea grease, for example, a tetraurea grease. The apparatus 200 comprises a series of eighteen (18) individual barrels (201 to 218) that are adjacent to one another and longitudinally connected to allow for the different operative steps to be sequentially performed and housing, for example a twin-screw element in a co-rotating configuration that runs through the entire length of the series of individual barrels. The series of barrels 201-218 comprise several zones. Barrel 201 comprises a first feeding zone. Barrel 202 comprises a second feeding zone. Barrels 203-206 comprise a first reacting-mixing zone. Barrels 207-208 comprise an optional venting zone. Barrel 209 comprises an oil-feeding zone. Barrels 210-211 comprise a first mixing zone. Barrel 212 comprises a second oil-feeding zone. Barrels 213-214 comprise a second mixing zone. Barrel 215 comprises a third oil-feeding zone. Barrel 216 comprises a third mixing zone. Barrels 217-218 may comprise a cooling-mixing zone. For example, if the resulting urea grease at barrel 217 is at a temperature and composition where no further cooling, mixing, or a combination thereof is desired, the cooling-mixing zone, for example, barrels 217-218, may be used to convey or transport the urea grease to a location where a urea grease may be obtained instead of being utilized as a cooling-mixing zone.

In an example process of the invention to provide for a tetraurea grease, a first feed component (A) comprising a base oil in first feeder 220 and a component having the formula OCN—R1—NCO, wherein R1 comprises a hydrocarbylene comprising from 2 to 30 carbon atoms, for example, methylene diisocyanate (4,4-diphenylmethane diisocyanate) (also referred to as MDI) in second feeder 222 are added to barrel 201. Optionally, the MDI may be added as flakes. Also optionally, the MDI may be combined with, for example, diluted with, base oil and added as a liquid. Also optionally, first feeder 220 and second feeder 222 may be combined as one feeder and the base oil and MDI may be added to barrel 201 as a blend. Also for example, one base oil feeder may be utilized to provide base oil to one or more locations using one or more pumps, pipes, valves, and combinations thereof instead of using several base oil feeders.

Base oil in third feeder 224 and one or more components, for example, a second feed component (B) comprising a monoamine having the formula NH2R2, wherein R2 comprises a hydrocarbyl comprising from 2 to 30 carbon atoms, for example, 1-octadecylamine, and another second feed component (C) comprising a diamine having the formula NH2R3NH2 wherein R3 comprises a hydrocarbylene comprising from 2 to 12 carbon atoms or a polyoxyhydrocarbylene comprising from 2 to 12 carbon atoms, for example, polyoxypropylene diamine (POD), preferably, component (B) and component (C) comprise a blend, in fourth feeder 226 are added to barrel 202. Optionally, third feeder 224 and fourth feeder 226 may be combined as one feeder and the base oil and component (B) and component (C) may be added to barrel 202 as a blend.

As the process continues through the barrels, a first reacting-mixing generally occurs in barrels 203-206. Venting of the resulting composition may be conducted utilizing vent 228 in barrels 207-208. Base oil in fifth feeder 230 is added to barrel 209. A mixing and, depending on the temperature of the base oil and barrel(s), generally a cooling, occurs in barrels 210-211. Base oil in sixth feeder 232 is added to barrel 212. A mixing and, depending on the temperature of the base oil and barrel(s), generally a cooling, occurs in barrels 213-214. Base oil, one or more additives, or a combination thereof, in seventh feeder 234 is added to barrel 215. A mixing and, depending on the temperature of the base oil, generally a cooling, occurs in barrel 216. The resulting composition is then passed to barrels 217-218 to provide for a cooled composition. If the resulting urea grease at barrel 217 is at a temperature and composition where no further cooling, mixing, or a combination thereof is desired, barrels 217-218 may be used to convey or transport the urea grease to a location where a urea grease may be obtained. A urea grease, for example, a tetraurea grease, may be obtained from barrel 218 and may be discharged to, for example, a storage container.

Optionally, the resulting composition may be passed from barrel 218 to additional iterations of barrels (not shown) comprising oil-feeding, additive-feeding, or a combination thereof, followed by mixing followed by a second cooling-mixing. Also optionally, the resulting composition may be passed from barrel 218 to urea grease processing apparatus (not shown) for example, a static mixer, a homogenizer, a screen pack, or a combination thereof.

Referring to FIG. 4, a schematic of an apparatus 300 is disclosed comprising a screw element, for example, a twin-screw co-rotating extruder, similar to the apparatus referred to herein in the EXAMPLES, to provide for a urea grease, for example, a diurea grease. The apparatus 300 comprises a series of eighteen (18) individual barrels (301 to 318) that are adjacent to one another and longitudinally connected to allow for the different operative steps to be sequentially performed and housing, for example a twin-screw element in a co-rotating configuration that runs through the entire length of the series of individual barrels. Barrels 301-303 may be dormant and not utilized, for example, when utilizing 15 barrels of an extruder comprising 18 barrels, or may not be present, for example when utilizing an extruder comprising 15 barrels where barrels 304-318 would be barrels 301-315, respectively. Barrels 304-318 comprise several zones. Barrel 304 comprises a first feeding zone. Barrel 305 comprises a second feeding zone. Barrels 306-307 comprise a first reacting-mixing zone. Barrel 308 comprises a third feeding zone. Barrel 309 comprises a second reacting-mixing zone. Barrel 310 comprises an optional venting zone. Barrel 311 comprises a first mixing zone. Barrel 312 comprises an oil-feeding zone. Barrels 313-314 comprise a second mixing zone. Barrel 315 comprises a second oil-feeding zone. Barrels 316-317 comprise a third mixing zone. Barrel 318 comprises a cooling-mixing zone. For example, if the resulting urea grease at barrel 317 is at a temperature and composition where no further cooling, mixing, or a combination thereof is desired, the cooling-mixing zone, for example, barrel 318, may be used to convey or transport the urea grease to a location where a urea grease may be obtained instead of being utilized as a cooling-mixing zone.

In an example process of the invention to provide for a diurea grease, a first feed component (A) comprising a base oil in first feeder 320 and a component having the formula OCN—R1—NCO, wherein R1 comprises a hydrocarbylene comprising from 2 to 30 carbon atoms, for example, methylene diisocyanate (4,4-diphenylmethane diisocyanate) (also referred to as MDI) in second feeder 322 are added to barrel 304. Optionally, the MDI may be added as flakes. Also optionally, the MDI may be combined with, for example, diluted with, base oil and added as a liquid. Also optionally, first feeder 320 and second feeder 322 may be combined as one feeder and the base oil and MDI may be added to barrel 304 as a blend. Also for example, one base oil feeder may be utilized to provide base oil to one or more locations using one or more pumps, pipes, valves, and combinations thereof instead of using several base oil feeders.

Second feed component (D) comprising a monoamine having the formula NH2R2, wherein R2 comprises a hydrocarbyl comprising from 2 to 30 carbon atoms, for example, octylamine, in third feeder 324 is added to barrel 305. As the process continues through the barrels, a first reacting-mixing generally occurs in barrels 306-307. Third feed component (E) comprising a monoamine having the formula NH2R2, wherein R2 comprises a hydrocarbyl comprising from 2 to 30 carbon atoms, for example, dodecylamine, in fourth feeder 326 is added to barrel 308.

As the process continues through the barrels, a second reacting-mixing generally occurs in barrel 309. Venting of the resulting composition may be conducted utilizing vent 328 in barrel 310. Mixing is conducted in barrel 311.

Base oil in fifth feeder 330 is added to barrel 312. A mixing and, depending on the temperature of the base oil and barrel(s), generally a cooling, occurs in barrels 313-314. Base oil in sixth feeder 332 is added to barrel 315. A mixing and, depending on the temperature of the base oil and barrel(s), generally a cooling, occurs in barrels 316-317. The resulting composition is then passed to barrel 318 to provide for a cooled composition. If the resulting urea grease at barrel 317 is at a temperature and composition where no further cooling, mixing, or a combination thereof is desired, barrel 318 may be used to convey or transport the urea grease to a location where a urea grease may be obtained. A urea grease, for example, a diurea grease, may be obtained from barrel 318 and may be discharged to, for example, a storage container.

Optionally, the resulting composition may be passed from barrel 318 to additional iterations of barrels (not shown) comprising oil-feeding, additive-feeding, or a combination thereof, followed by mixing followed by second cooling-mixing. Also optionally, the resulting composition may be passed from barrel 318 to urea grease processing apparatus (not shown) for example, a static mixer, a homogenizer, a screen pack, or a combination thereof.

Examples

Example processes of the invention were conducted using a 34-mm twin-screw co-rotating extruder from Coperion Werner and Pfleiderer, Stuttgart, Germany, having model number ZSK34MV to prepare tetraurea greases and diurea greases. Table 1 discloses formulations of tetraurea greases and diurea greases that were prepared. HVI 160B and HVI 650 refer to base oils commercially available from member companies of the Shell Group.

TABLE 1

Urea Greases

| Compound | Tetraurea grease (wt %) | Diurea grease (wt %) |
|---|---|---|
| MDI (methylene diisocyanate)(4,4'-diphenylmethane diisocyanate) (Rhein Chemie, Mannheim, Germany) | 4.85 | 5.81 |
| 1-Octadecylamine (C18 amine)(Armeen 18D from Akzo Nobel Surface Chemistry, Chicago, Illinois, USA) | 8.3 | — |
| Polyoxypropylene diamine (Jeffamine D230 from Huntsman Chemical, The Woodlands, Texas, USA) | 0.85 | — |
| Octylamine (C8 amine)(Genamin 8R 100D from Clariant, Sulzbach am Taunus, Germany) | — | 4.61 |
| Dodecylamine (C12 amine) (Genamin 12R 100D from Clariant, Sulzbach am Taunus, Germany) | — | 1.68 |
| Additives package | 3.5 | 5.25 |
| Base Oil | 82.5 (HVI 160B) | 82.65 (HVI 160B and HVI 650) (ingredients were diluted in HVI 160B; reaction oil and dilution oil were HVI 650) |
| Total | 100.0 | 100.0 |

Characteristics of the extruder are disclosed in Table 2.

TABLE 2

| | |
|---|---|
| Screw length: | 2268 mm |
| Barrel length: | 126 mm |
| Number of barrels: | 18 |
| Barrel heating: | Electrical |
| Barrel cooling: | Water |

The reactive ingredients were diluted in base oil and injected as liquids into the extruder using gear pumps (Cipex from Maag Pump Systems Textron A.G., Zurich, Switzerland). The dilution rates of the different ingredients are disclosed in Table 3. The lines and vessels were insulated due to the use of melt ingredients (MDI, solid amines at room temperature) and to avoid plugging of the feeding system. Warm oil was first injected in the lines before pumping the ingredients that could have solidified at reduced temperatures. Supplementary oil feeds were injected and are referred to herein as "reaction oil" when the oil was injected with the ingredients prior to the chemical reaction and are referred to herein as "dilution oil" when injected after the chemical reaction to provide, for example, for a cooling and dilution of the grease (for example in barrels 9, 12, 15, or a combination thereof).

TABLE 3

Dilution rates of ingredients

| Compounds | Dilution rate (type of base oil) |
|---|---|
| 1/Tetraurea base grease | |
| MDI | 14.7 wt % (HVI 160B) |
| C18 amine (Armeen 18D) | 29.0 wt % (HVI 160B) |
| Diamine (Jeffamine D230) | 2.98 wt % (HVI 160B) |
| 2/Diurea base grease | |
| MDI | 17.0 wt % (HVI 160B) |
| C8 amine (Genamin 8R 100D) | 33.0 wt % (HVI 160B) |
| C12 amine (Genamin 12R 100D) | 33.0 wt % (HVI 160B) |

Procedure Utilized to Start the Test Runs:

Warmed the lines for the melt ingredients (MDI, solid amines at room temperature) with pre-heated (80° C.) flush oil (preheating oil)

Started reaction oil

Stopped preheating oil and started amines feeding

Stopped preheating oil and started MDI feeding

Started dilution oil

Procedure Utilized to Stop the Test Runs:

Stopped MDI feeding, flushed lines with warm oil

Stopped amines feeding, flushed lines with warm oil

Maintained flush oil for 10 minutes

To check that a complete reaction was achieved, the total amine number was measured by titration in a manner similar to ASTM D2076. A sample was dissolved in Petroleum Spirit and was titrated with 0.1N alcoholic hydrochloric acid in the presence of Bromocresol Green indicator. Excess MDI was determined by Fourier Transform Infra Red (FTIR). Unreacted diisocyanate was determined by examination of the infrared isocyanate peak at approximately 2250 cm$^{-1}$.

Tetraurea Grease:

The ingredients preparation that was utilized for preparing tetraurea grease is disclosed in Table 4. The ingredients were diluted in HVI 160B base oil. HVI 160B base oil was injected as reaction oil and dilution oil.

TABLE 4

| | |
|---|---|
| Diluted MDI | Charged oil (HVI 160B base oil) to the vessel and heated to 60° C. Charged MDI to the vessel and agitated for 15 to 20 minutes until MDI melted. Maintained heating and stirring of the vessel during the production. |
| Diluted Amines | Charged oil (HVI 160B base oil) to the vessel and heated to 60° C. Charged the preheated C18 amine and the liquid diamine to the vessel. Continued heating vessel to 80° C. and agitated for 15 to 20 minutes until the amines melted. Maintained heating and stirring of the vessel during the production. |

TABLE 4-continued

| | |
|---|---|
| Reaction oil (HVI 160B base oil) | Preheated at 60° C. |
| Dilution oil (HVI 160B base oil) | Preheated at 50° C. |

The vessels were insulated tanks that were each equipped with an electrical heater and a stirring system comprising two propellers located at different heights on the axle.
The extruder layout for the tetraurea grease comprised:
  Barrel no. 1: diluted MDI and base oil-feeding (conveying elements)
  Barrel no. 2: diluted amines feeding (conveying elements)
  Barrels no. 3 to 6: reacting/mixing/transporting
  Barrels no. 7 and 8: optional venting zone (barrel may be opened)
  Barrel no. 9: optional feeding/injecting of dilution oil
  Barrels no. 10 and 11: mixing/cooling/transporting
  Barrel no. 12: optional feeding/injecting of dilution oil
  Barrels no. 13 and 14: mixing/cooling/transporting
  Barrel no. 15: optional feeding/injecting of dilution oil, one or more additives, or a combination thereof
  Barrel no. 16: mixing
  Barrels no. 17 to 18: transporting/discharging
The screw configuration (Screw Configuration 1) utilized for preparing a tetraurea grease is disclosed in Table 5.

TABLE 5

Screw Configuration 1
(tetraurea grease)

| Position | Element | Pitch | Length | Running Total | Barrel | Barrel Position |
|---|---|---|---|---|---|---|
| 1 | 28/14 | 28 | 14 | 14 | BBL1 | |
| 2 | 42/42 | 42 | 42 | 56 | | |
| 3 | 42/42 | 42 | 42 | 98 | | |
| 4 | 42/42 | 42 | 42 | 140 | BBL2 | 126 |
| 5 | 28/28 | 28 | 28 | 168 | | |
| 6 | 28/28 | 28 | 28 | 196 | | |
| 7 | 28/28 | 28 | 28 | 224 | | |
| 8 | KB 45/5/28 | | 28 | 252 | BBL3 | 252 |
| 9 | KB 45/5/14 | | 14 | 266 | | |
| 10 | KB 45/5/14 Li | | 14 | 280 | | |
| 11 | 28/14 | 28 | 14 | 294 | | |
| 12 | KB 45/5/28 | | 28 | 322 | | |
| 13 | KB 45/5/28 | | 28 | 350 | | |
| 14 | 28/28 | 28 | 28 | 378 | BBL4 | 378 |
| 15 | 28/28 | 28 | 28 | 406 | | |
| 16 | 28/28 | 28 | 28 | 434 | | |
| 17 | 28/28 | 28 | 28 | 462 | | |
| 18 | 28/28 | 28 | 28 | 490 | | |
| 19 | KB 45/5/14 | | 14 | 504 | BBL5 | 504 |
| 20 | KB 45/5/14 | | 14 | 518 | | |
| 21 | KB 45/5/14 Li | | 14 | 532 | | |
| 22 | 28/28 | 28 | 28 | 560 | | |
| 23 | 28/28 | 28 | 28 | 588 | | |
| 24 | 28/28 | 28 | 28 | 616 | | |
| 25 | KB 45/5/28 | | 28 | 644 | BBL6 | 630 |
| 26 | KB 45/5/28 | | 28 | 672 | | |
| 27 | KB 45/5/28 | | 28 | 700 | | |
| 28 | KB 45/5/28 | | 28 | 728 | | |
| 29 | KB 45/5/14 Li | | 14 | 742 | | |
| 30 | KB 45/5/14 Li | | 14 | 756 | BBL7 | 756 |
| 31 | 42/42 | 42 | 42 | 798 | | |
| 32 | 42/42 | 42 | 42 | 840 | | |
| 33 | 42/42 | 42 | 42 | 882 | BBL8 | 882 |
| 34 | 42/42 | 42 | 42 | 924 | | |
| 35 | 42/42 | 42 | 42 | 966 | | |
| 36 | 42/42 | 42 | 42 | 1008 | BBL9 | 1008 |
| 37 | 42/42 | 42 | 42 | 1050 | | |
| 38 | 42/21 | 42 | 21 | 1071 | | |
| 39 | 28/28 | 28 | 28 | 1099 | | |
| 40 | 28/28 | 28 | 28 | 1127 | BBL10 | 1134 |
| 41 | KB 45/5/28 | | 28 | 1155 | | |
| 42 | KB 45/5/28 | | 28 | 1183 | | |
| 43 | Spacer | | 1 | 1184 | | |
| 44 | ZME 6.5/13 | | 13 | 1197 | | |
| 45 | ZME 6.5/13 | | 13 | 1210 | | |
| 46 | Spacer | | 1 | 1211 | | |
| 47 | KB 45/5/28 | | 28 | 1239 | | |
| 48 | 28/28 | 28 | 28 | 1267 | BBL11 | 1260 |
| 49 | 28/28 | 28 | 28 | 1295 | | |
| 50 | KB 45/5/28 | | 28 | 1323 | | |
| 51 | KB 45/5/28 | | 28 | 1351 | | |
| 52 | KB 45/5/14 Li | | 14 | 1365 | | |
| 53 | KB 45/5/14 Li | | 14 | 1379 | BBL12 | 1386 |
| 54 | 42/42 | 42 | 42 | 1421 | | |
| 55 | 42/42 | 42 | 42 | 1463 | | |
| 56 | 42/42 | 42 | 42 | 1505 | BBL13 | 1512 |
| 57 | KB 45/5/28 | | 28 | 1533 | | |
| 58 | KB 45/5/28 | | 28 | 1561 | | |
| 59 | Spacer | | 1 | 1562 | | |
| 60 | ZME 6.5/13 | | 13 | 1575 | | |
| 61 | ZME 6.5/13 | | 13 | 1588 | | |
| 62 | Spacer | | 1 | 1589 | | |
| 63 | KB 45/5/28 | | 28 | 1617 | | |
| 64 | KB 45/5/28 | | 28 | 1645 | BBL14 | 1638 |
| 65 | KB 45/5/14 Li | | 14 | 1659 | | |
| 66 | 42/21 | 42 | 21 | 1680 | | |
| 67 | 28/28 | 28 | 28 | 1708 | | |
| 68 | KB 45/5/28 | | 28 | 1736 | | |
| 69 | KB 45/5/28 | | 28 | 1764 | BBL15 | 1764 |
| 70 | 42/42 | 42 | 42 | 1806 | | |
| 71 | 42/42 | 42 | 42 | 1848 | | |
| 72 | 42/21 | 42 | 21 | 1869 | | |
| 73 | 28/28 | 28 | 28 | 1897 | BBL16 | 1890 |
| 74 | 28/28 | 28 | 28 | 1925 | | |
| 75 | KB 45/5/28 | | 28 | 1953 | | |
| 76 | KB 45/5/14 | | 14 | 1967 | | |
| 77 | KB 45/5/14 | | 14 | 1981 | | |
| 78 | KB 45/5/14 Li | | 14 | 1995 | | |
| 79 | KB 45/5/14 Li | | 14 | 2009 | BBL17 | 2016 |
| 80 | 42/42 | 42 | 42 | 2051 | | |
| 81 | 42/42 | 42 | 42 | 2093 | | |
| 82 | 42/21 | 42 | 21 | 2114 | | |
| 83 | 42/21 | 42 | 21 | 2135 | | |
| 84 | 42/21 | 42 | 21 | 2156 | BBL18 | 2142 |
| 85 | 42/21 | 42 | 21 | 2177 | | |
| 86 | 42/21 | 42 | 21 | 2198 | | |
| 87 | 28/28 | 28 | 28 | 2226 | | |
| 88 | 28/28 | 28 | 28 | 2254 | | |
| 89 | 28/14 | 28 | 14 | 2268 | | |

The temperature profile disclosed in Table 6 was obtained for Screw Configuration 1 and was used throughout the test runs for preparing a tetraurea grease.

TABLE 6

| Barrel | 1 | 2 | 3 | 4 | 5 | 6 | 7 | 8 | 9 |
|---|---|---|---|---|---|---|---|---|---|
| Temp. (° C.) | 80 | 80 | 110 | 150 | 170 | 170 | 170 | 150 | 130 |

| Barrel | 10 | 11 | 12 | 13 | 14 | 15 | 16 | 17 | 18 |
|---|---|---|---|---|---|---|---|---|---|
| Temp. (° C.) | 115 | 110 | 100 | 90 | 80 | 75 | 60 | 60 | 60 |

A tetraurea base grease was obtained at different throughputs ranging from 30 kilograms per hour (kg/hr) to 43 kg/hr and at different screw speeds ranging from 320 revolutions per minute (rpm) to 600 rpm (information is disclosed in Table 7). Basic properties were obtained for the tetraurea base grease and are disclosed in Table 8.

TABLE 7

| Test Run no. | MDI + oil (kg/hr) | Amines + oil (kg/hr) | Reaction oil (kg/hr) | Dilution oil (kg/hr) | Total throughput (kg/hr) | Thickener content (barrels 3 to 6) (wt. %) (calculated) | Thickener content in base grease (wt. %) (calculated) | Screw speed (rpm) |
|---|---|---|---|---|---|---|---|---|
| 1 | 11.5 | 10 | 5.9 | 4.7 (1) | 32.1 | 17.8 | 15.2 | 320 |
| 2 | 11.5 | 10 | 5.9 | 4.7 (1) | 32.1 | 17.8 | 15.2 | 600 |
| 3 | 11.5 | 10 | 5.9 | 2.6 (1) | 30.0 | 17.8 | 16.3 | 320 |
| 4 | 11.5 | 10 | 5.9 | 6.7 (1) | 34.1 | 17.8 | 14.3 | 600 |
| 5 | 11.5 | 10 | 0 | 10.6 (2) | 32.1 | 22.7 | 15.2 | 320 |
| 6 | 11.5 | 10 | 0 | 10.6 (2) | 32.1 | 22.7 | 15.2 | 600 |
| 7 | 16.1 | 14 | 0 | 10.6 (2) | 40.7 | 22.7 | 16.8 | 600 |
| 8 | 16.1 | 14 | 0 | 12.7 (2) | 42.8 | 22.7 | 16 | 600 |

(1) Dilution oil injected in barrel no. 12
(2) Dilution oil injected in barrels no. 9 (36.8 wt %) and no. 12 (63.2 wt %)

TABLE 8

Tetraurea base grease properties

| Test Run No. | Method | 1 | 4 | 5 | 6 | 7 | 8 |
|---|---|---|---|---|---|---|---|
| Throughput (kg/h) | — | 32.1 | 34.1 | 32.1 | 32.1 | 40.7 | 42.8 |
| Screw speed (rpm) | — | 320 | 600 | 320 | 600 | 600 | 600 |
| FTIR MDI peak at 2250 cm$^{-1}$ | — | None | None | None | None | None | None |
| Amine Number (mg KOH/g) | Titration (similar to ASTM D2076) | 0.02 | 0.03 | 0.02 | 0.02 | 0.02 | 0.03 |
| Dropping point, °C. | ASTM D566 | 265 | 267 | 261 | 265 | 277 | 273 |
| Unworked penetration at 25° C., dmm | ASTM D217 | 320 | 306 | 346 | 308 | 275 | 298 |
| Worked penetration at 25° C. (60 strokes), dmm | ASTM D217 | 299 | 311 | 340 | 316 | 275 | 309 |
| Delta penetration, (Worked/60 strokes minus Unworked), dmm | — | −21 | 5 | −6 | 8 | 0 | 11 |
| Worked penetration at 25° C. (100,000 strokes), dmm | ASTM D217 | 312 | 293 | 318 | 321 | 292 | 316 |

The tetraurea base grease from Test Run No. 1 (Grease Sample No. 1) was treated with an additives package to provide for a tetraurea finished grease. 100 grams of the tetraurea base grease (Grease Sample No. 1) were removed and heated to 85° C. and solid additives were dispersed into the tetraurea base grease using a laboratory mixer. The tetraurea grease was then milled three times using a triple-roll mill until the solids were dispersed. The milled sample was placed into a Hobart mixer with the remaining grease (1448 grams) and the solid and liquid additives. The grease sample was mixed for 45 minutes at 85° C. The grease sample was then milled using an APV Gaulin mill at low pressure to provide for a tetraurea finished grease (Grease Sample No. 2).

Basic properties were obtained for the tetraurea finished grease and are disclosed in Table 9.

TABLE 9

| | Units | Tetraurea finished grease (Grease Sample No. 2) | Typical tetraurea grease |
|---|---|---|---|
| Tetraurea base grease (Grease Sample No. 1) | wt % | 96.5 | — |
| Additives package | wt % | 3.5 | — |
| Unworked penetration at 25° C., ASTM D217 | dmm | 268 | — |
| Worked penetration at 25° C. (60 Strokes), ASTM D217 | dmm | 298 | 285 |
| Dropping point, ASTM D566 | °C. | 260 | >232 |
| Ball bearing at 177° C., ASTM D3336 Grease life, average | hours | 436 | 435 |

Diurea Grease:

The ingredients preparation that was utilized to prepare a diurea grease is disclosed in Table 10. The ingredients were diluted in HVI 160B base oil. HVI 650 base oil was injected as reaction oil and dilution oil.

TABLE 10

| Diluted MDI | Charged oil (HVI 160B base oil) to the vessel and heated to 60° C. Charged MDI to the vessel and agitated for 15 to 20 minutes until MDI melted. Maintained heating and stirring of the vessel during the production. |
|---|---|

TABLE 10-continued

| | |
|---|---|
| Diluted C8 amine | Charged oil (HVI 160B base oil) to the vessel and heated to 50° C. Charged the C8 amine to the vessel and agitated for 15 to 20 minutes. Maintained heating and stirring of the vessel during the production. |
| Diluted C12 amine | Charged oil (HVI 160B base oil) to the vessel and heated to 80° C. Charged the preheated C12 amine to the vessel and agitated until the amines melted. Maintained heating and stirring of the vessel during the production. |
| Reaction oil (HVI 650 base oil) | Preheated at 60° C. |
| Dilution oil (HVI 650 base oil) | Preheated at 50° C. |

The vessels were insulated tanks that were each equipped with an electrical heater and a stirring system comprising two propellers located at different heights on the axle.

The diurea grease trials on the ZSK34MV extruder utilized 15 of 18 barrels. Three dormant barrels were present at the beginning of the extruder just before the first feeding zone and included only conveying elements.

For the manufacture of the diurea grease, the feeding/injection points for the two amines were kept separate from each other. It was discovered that the distance between the two feeding/injection points, for example, 336 mm, in the ZSK34MV extruder should be enough to obtain urea greases comprising properties as disclosed herein.

The extruder layout for the diurea base grease comprised:
- Barrel nos. 1 to 3: dormant barrels (only conveying elements)
- Barrel no. 4: diluted MDI and reaction oil-feeding (conveying elements)
- Barrel no. 5: first diluted amine injection (conveying elements)
- Barrels nos. 6 and 7: reacting/mixing/transporting
- Barrel no. 8: second diluted amine injection
- Barrel no. 9: reacting/mixing/transporting
- Barrel no. 10: optional venting zone (barrel may be opened)
- Barrel no. 11: mixing
- Barrel no. 12: optional feeding/injecting of dilution oil
- Barrel nos. 13 and 14: mixing/cooling/transporting
- Barrel no. 15: injecting of dilution oil, one or more additives, or a combination thereof
- Barrel no. 16: mixing
- Barrels nos. 17 to 18: transporting/discharging The screw configuration (Screw Configuration 2) utilized for preparing the diurea grease is disclosed in Table 11.

TABLE 11

Screw Configuration 2
(diurea grease)

| Position | Element | Pitch | Length | Running Total | Barrel | Barrel Position |
|---|---|---|---|---|---|---|
| 1 | 28/14 | 28 | 14 | 14 | BBL1 | |
| 2 | 28/14 | 28 | 14 | 28 | | |
| 3 | 28/28 | 28 | 28 | 56 | | |
| 4 | 28/28 | 28 | 28 | 84 | | |
| 5 | 42/42 | 42 | 42 | 126 | BBL2 | 126 |
| 6 | 42/42 | 42 | 42 | 168 | | |
| 7 | 42/42 | 42 | 42 | 210 | | |
| 8 | 42/42 | 42 | 42 | 252 | BBL3 | 252 |
| 9 | 42/21 | 42 | 21 | 273 | | |
| 10 | 42/21 | 42 | 21 | 294 | | |
| 11 | 42/21 | 42 | 21 | 315 | | |
| 12 | 42/21 | 42 | 21 | 336 | | |
| 13 | 42/42 | 42 | 42 | 378 | BBL4 | 378 |
| 14 | 42/42 | 42 | 42 | 420 | | |
| 15 | 42/42 | 42 | 42 | 462 | | |
| 16 | 42/42 | 42 | 42 | 504 | BBL5 | 504 |
| 17 | 42/42 | 42 | 42 | 546 | | |
| 18 | 42/21 | 42 | 21 | 567 | | |
| 19 | 28/28 | 28 | 28 | 595 | | |
| 20 | 28/28 | 28 | 28 | 623 | | |
| 21 | KB 45/5/28 | | 28 | 651 | BBL6 | 630 |
| 22 | KB 45/5/28 | | 28 | 679 | | |
| 23 | KB 45/5/14 | | 14 | 693 | | |
| 24 | KB 45/5/14 | | 14 | 707 | | |
| 25 | KB 45/5/14 Li | | 14 | 721 | | |
| 26 | KB 45/5/14 Li | | 14 | 735 | | |
| 27 | 42/42 | 42 | 42 | 777 | BBL7 | 756 |
| 28 | KB 45/5/28 | | 28 | 805 | | |
| 29 | KB 45/5/28 | | 28 | 833 | | |
| 30 | 28/28 | 28 | 28 | 861 | | |
| 31 | 42/42 | 42 | 42 | 903 | BBL8 | 882 |
| 32 | 42/42 | 42 | 42 | 945 | | |
| 33 | 42/42 | 42 | 42 | 987 | | |
| 34 | 28/28 | 28 | 28 | 1015 | BBL9 | 1008 |
| 35 | KB 45/5/28 | | 28 | 1043 | | |
| 36 | KB 45/5/28 | | 28 | 1071 | | |
| 37 | KB 45/5/14 | | 14 | 1085 | | |
| 38 | KB 45/5/14 Li | | 14 | 1099 | | |
| 39 | 42/42 | 42 | 42 | 1141 | BBL10 | 1134 |
| 40 | 42/42 | 42 | 42 | 1183 | | |
| 41 | 42/42 | 42 | 42 | 1225 | | |
| 42 | 42/21 | 42 | 21 | 1246 | | |
| 43 | 42/21 | 42 | 21 | 1267 | BBL11 | 1260 |
| 44 | KB 45/5/28 | | 28 | 1295 | | |
| 45 | KB 45/5/28 | | 28 | 1323 | | |
| 46 | KB 45/5/14 Li | | 14 | 1337 | | |
| 47 | 28/28 | 28 | 28 | 1365 | | |
| 48 | 28/28 | 28 | 28 | 1393 | BBL12 | 1386 |
| 49 | 42/42 | 42 | 42 | 1435 | | |
| 50 | 42/42 | 42 | 42 | 1477 | | |
| 51 | KB 45/5/28 | | 28 | 1505 | | |
| 52 | KB 45/5/28 | | 28 | 1533 | BBL13 | 1512 |
| 53 | KB 45/5/14 | | 14 | 1547 | | |
| 54 | 28/28 | 28 | 28 | 1575 | | |
| 55 | 28/28 | 28 | 28 | 1603 | | |
| 56 | KB 45/5/28 | | 28 | 1631 | | |
| 57 | KB 45/5/28 | | 28 | 1659 | BBL14 | 1638 |
| 58 | KB 45/5/14 Li | | 14 | 1673 | | |
| 59 | Spacer | | 1 | 1674 | | |
| 60 | ZME 6.5/13 | | 13 | 1687 | | |
| 61 | ZME 6.5/13 | | 13 | 1700 | | |
| 62 | Spacer | | 1 | 1701 | | |
| 63 | KB 45/5/28 | | 28 | 1729 | | |
| 64 | KB 45/5/28 | | 28 | 1757 | | |
| 65 | KB 45/5/14 Li | | 14 | 1771 | BBL15 | 1764 |
| 66 | 28/28 | 28 | 28 | 1799 | | |
| 67 | 28/28 | 28 | 28 | 1827 | | |
| 68 | KB 45/5/28 | | 28 | 1855 | | |
| 69 | KB 45/5/28 | | 28 | 1883 | | |
| 70 | KB 45/5/14 Li | | 14 | 1897 | BBL16 | 1890 |
| 71 | 28/28 | 28 | 28 | 1925 | | |
| 72 | 28/28 | 28 | 28 | 1953 | | |
| 73 | KB 45/5/28 | | 28 | 1981 | | |
| 74 | KB 45/5/14 | | 14 | 1995 | | |
| 75 | KB 45/5/14 Li | | 14 | 2009 | | |
| 76 | 28/28 | 28 | 28 | 2037 | BBL17 | 2016 |
| 77 | 28/28 | 28 | 28 | 2065 | | |
| 78 | KB 45/5/28 | | 28 | 2093 | | |
| 79 | KB 45/5/14 Li | | 14 | 2107 | | |
| 80 | 42/21 | 42 | 21 | 2128 | BBL18 | 2142 |
| 81 | 42/21 | 42 | 21 | 2149 | | |
| 82 | 42/21 | 42 | 21 | 2170 | | |
| 83 | 28/28 | 28 | 28 | 2198 | | |

TABLE 11-continued

Screw Configuration 2
(diurea grease)

| Position | Element | Pitch | Length | Running Total | Barrel | Barrel Position |
|---|---|---|---|---|---|---|
| 84 | 28/28 | 28 | 28 | 2226 | | |
| 85 | 28/28 | 28 | 28 | 2254 | | |
| 86 | 28/14 | 28 | 14 | 2268 | | |

The temperature profile disclosed in Table 12 was obtained for Screw Configuration 2 and was used throughout the test runs for preparing a diurea grease.

TABLE 12

| Barrel | 1 | 2 | 3 | 4 | 5 | 6 | 7 | 8 | 9 |
|---|---|---|---|---|---|---|---|---|---|
| Temp. (° C.) | 60 | 60 | 60 | 60 | 80 | 100 | 150 | 150 | 190 |
| Barrel | 10 | 11 | 12 | 13 | 14 | 15 | 16 | 17 | 18 |
| Temp. (° C.) | 185 | 150 | 130 | 90 | 80 | 80 | 80 | 80 | 80 |

A diurea base grease was obtained at different throughputs ranging from 45 kg/hr to 60 kg/hr and at different screw speeds ranging from 300 rpm to 600 rpm (information is disclosed in Table 13). Basic properties were obtained for the diurea base grease and are disclosed in Table 13.

TABLE 13

Diurea base grease properties

| Test Run No. | 9 | 10 | 11 | 12 | 13 | 14 | 15 | 16 |
|---|---|---|---|---|---|---|---|---|
| Flow rates, kg/hr | | | | | | | | |
| Total | 45 | 50 | 50 | 50 | 50 | 60 | 60 | 55.5 |
| Diluted MDI | 19.0 | 19.0 | 19.0 | 19.0 | 19.0 | 22.6 | 22.6 | 22.6 |
| Diluted C8 amine | 7.8 | 7.8 | 7.8 | 7.8 | 7.8 | 9.5 | 9.5 | 9.5 |
| Diluted C12 amine | 2.8 | 2.8 | 2.8 | 2.8 | 2.8 | 3.5 | 3.5 | 3.5 |
| Reaction oil | 7.9 | 7.9 | 7.9 | 7.9 | 7.9 | 7.9 | 7.9 | 7.9 |
| Dilution oil | 7.5 | 12.4 | 12.4 | 12.4 | 12.4 | 16.6 | 16.6 | 12.0 |
| Thickener content in base grease (wt. %) (calculated) | 15.0 | 13.5 | 13.5 | 13.5 | 13.5 | 13.5 | 13.5 | 14.7 |
| Process conditions | | | | | | | | |
| Screw speed, rpm | 500 | 300 | 400 | 500 | 600 | 400 | 500 | 600 |
| MDI peak - IR | none | none | none | none | none | vsp* | none | none |
| Amine value, mg KOH/g | 0.003 | 0 | 0.002 | 0.002 | 0 | 0.002 | 0.005 | 0.004 |
| Dropping point, ° C. | 297 | 295 | 292 | 295 | 296 | 294 | 292 | 295 |
| Unworked penetration at 25° C., dmm, ASTM D217 | 289 | 347 | 328 | 323 | 303 | 342 | 330 | 294 |
| Worked penetration at 25° C. (60 strokes), dmm, ASTM D217 | 271 | 327 | 314 | 313 | 293 | 328 | 315 | 279 |
| Delta penetration, (worked/60 strokes minus unworked), dmm | −18 | −20 | −14 | −10 | −10 | −14 | −15 | −15 |

*very small peak

The diurea base grease from Test Run No. 9 and Test Run No. 12 were treated with an additives package. 100 grams of the diurea base grease were removed and heated to 120° C. and solid additives were dispersed into the diurea base grease and was then added to the bulk of the grease (2800 grams) using a laboratory mixer. The diurea grease was then milled once using a triple-roll mill.

Basic properties were obtained for the diurea finished grease (Grease Sample No. 3) using the diurea base grease from Test Run No. 9 and for the diurea finished grease (Grease Sample No. 4) using the diurea base grease from Test Run No. 12 and are disclosed in Table 14.

TABLE 14

Diurea finished grease properties

| Tests | Method | Grease Sample No. 3 | Grease Sample No. 4 | Typical Diurea Grease |
|---|---|---|---|---|
| Appearance | visual | Homogeneous | Homogeneous | — |
| Color | visual | Pale Lemon | Pale Lemon | — |
| Unworked penetration at | ASTM | 255 | 260 | 267 |

TABLE 14-continued

Diurea finished grease properties

| Tests | Method | Grease Sample No. 3 | Grease Sample No. 4 | Typical Diurea Grease |
|---|---|---|---|---|
| 25° C., dmm | D217 | | | |
| Worked penetration at 25° C. (60 strokes), dmm | ASTM D217 | 269 | 267 | 279 |
| Delta penetration, (worked/60 strokes minus unworked), dmm | ASTM D217 | +14 | +7 | +12 |
| Oil separation (18 hrs at 40° C.), wt % | IP 121 | 0.0 | 0.0 | 0.1 |
| Dropping point, ° C. | ASTM D566 | 265 | 264 | 266 |
| Roll stability (18 hrs at 65° C.), dmm | ASTM D1831 | +102 [371] | +94 [361] | — |
| EP 4-ball weld load, kgf | ASTM D2596 | 270 | 280 | 300 |
| Oxidation stability (100° C.; 100 hrs), kPa | ASTM D942 | 41.4/34.5 | 48.3/51.7 | 24 |
| EP 4-ball wear scar (40 kg; 75° C.; 1200 rpm), mm | | 0.49 | 0.49 | 0.50 |
| Roll stability (100 hrs at 100° C.), dmm | ASTM D1831 | +67 [336] | +75 [342] | +75 |
| Emcor rust test (distilled water), Rating | IP 220 | 0/0 | 0/0 | 0/0 |
| Emcor rust test (salt water), Rating | IP 220 | 3/3 | 3/3 | 4/4 |
| Oil separation (7 days at 40° C.), wt % | IP 121 | 0.94 | 0.83 | 0.7 |
| Worked penetration at 25° C. (100,000 strokes), dmm | ASTM D217 | 317 | 304 | 322 |
| Delta Penetration, (worked/100,000 strokes minus worked/60 strokes), dmm | ASTM D217 | +48 | +37 | +43 |
| Worked penetration at 25° C. (100,000 strokes + 10% Distilled water), dmm | ASTM D217 | 336 | 342 | 320 |
| Delta Penetration, (worked/100,000 strokes + 10% Distilled Water minus worked/60 strokes), dmm | ASTM D217 | +67 | +75 | +41 |
| Water wash out (1 hr, 79° C.), wt % | ASTM D1264 | 2.0/1.5 | 1.0/0.0 | — |

What is claimed is:

1. A continuous process for preparing a urea grease comprising:
providing an apparatus comprising an extruder and a plurality of zones arranged in series and in fluid communication, wherein the plurality of zones comprise (a) a first feeding zone; (b) a second feeding zone; (c) a first reacting-mixing zone; and (d) a cooling-mixing zone, and wherein the zones are in the order (a), (b), (c), (d);
introducing a first feed component to the first feeding zone (a), wherein the first feed component comprises a diisocyanate;
introducing a second feed component to the second feeding zone (b), wherein the second feed component comprises at least one component selected from the group consisting of: a monoamine, a diamine, an alcohol, and a combination thereof;
allowing the first feed component and the second feed component to react and mix within the first reacting-mixing zone (c);
allowing the output from the first reacting-mixing zone (c) to be cooled and mixed within the cooling-mixing zone (d); and
thereby obtaining the urea grease.

2. A process according to claim 1 wherein the apparatus further comprises an oil-feeding zone downstream of the first reacting-mixing zone (c) and further comprising introducing an oil feed to the oil-feeding zone.

3. A process according to claim 1 wherein the apparatus further comprises at least one additional mixing zone.

4. A process according to claim 1 wherein the second feed component comprises at least one component selected from the group consisting of: a monoamine, a diamine, and a combination thereof, and wherein the urea grease comprises a tetraurea grease.

5. A continuous process for preparing a urea grease comprising:
providing an apparatus comprising an extruder and a plurality of zones arranged in series and in fluid communication, wherein the plurality of zones comprise (a) a first feeding zone; (b) a second feeding zone; (c) a first reacting-mixing zone; (d) a third feeding zone; (e) a second reacting-mixing zone; and (f) a cooling-mixing zone, and wherein the zones are in the order (a), (b), (c), (d), (e), (f);
introducing a first feed component to the first feeding zone (a), wherein the first feed component comprises a diisocyanate having the formula OCN—R1-NCO and wherein R1 comprises a hydrocarbylene comprising from 2 to 30 carbon atoms;

introducing a second feed component to the second feeding zone (b), wherein the second feed component comprises at least one component selected from the group consisting of: a monoamine, a diamine, an alcohol, and a combination thereof;

allowing the first feed component and the second feed component to react and mix within the first reacting-mixing zone (c);

introducing a third feed component to the third feeding zone (d), wherein the third feed component comprises at least one component selected from the group consisting of: a monoamine, a diamine, and a combination thereof;

allowing the output from the first reacting-mixing zone (c) to react and mix with the third feed component within the second reacting-mixing zone (e);

allowing the output from the second reacting-mixing zone (e) to be cooled and mixed within the cooling-mixing zone (f); and thereby obtaining the urea grease.

6. A process according to claim 5 wherein the apparatus further comprises an oil-feeding zone downstream of the second reacting-mixing zone (e) and further comprising introducing an oil feed to the oil-feeding zone.

7. A process according to claim 5 wherein the apparatus further comprises at least one additional mixing zone.

8. A process according to claim 5 wherein the urea grease comprises a diurea grease.

9. A process according to claim 1 wherein the second feed component comprises a monoamine, and wherein the urea grease comprises a diurea grease.

10. A process according to claim 1 wherein the diisocyanate is selected from the group consisting of: diphenylmethane diisocyanate, phenylene diisocyanate, diphenyl diisocyanate, phenyl diisocyanate, naphthylene diisocyanate, tolylene orthodiisocyanate, tolylene diisocyanate, and a combination thereof.

11. A process according to claim 1 wherein the monoamine is selected from the group consisting of: octylamine, dodecylamine, tetradecylamine, hexadecylamine, octadecylamine, oleylamine, aniline, benzyl amine, p-toluidine, p-chloro-aniline, m-xylidine, and a combination thereof.

12. A process according to claim 1 wherein the diamine is selected from the group consisting of: ethylenediamine, propylenediamine, butylenediamine, pentylenediamine, hexamethylenediamine, polyoxymethylene diamine, polyoxyethylene diamine, polyoxypropylene diamine, polyoxyisopropylene diamine, polyetheramine, triethylene glycol diamine, and a combination thereof.

13. A process according to claim 1 wherein the alcohol is selected from the group consisting of: 1-dodecanol, 1-tetradecanol, 1-hexadecanol, 1-octadecanol, cis-9-octadecen-1-ol, 9-octadecadien-1-ol, 12-octadecadien-1-ol, and a combination thereof.

14. A process according to claim 1 wherein the first feed component further comprises a base oil.

15. A process according to claim 1 wherein the second feed component further comprises a base oil.

16. A process according to claim 5 wherein the second feed component comprises an alcohol, and wherein the urea grease comprises a triurea-urethane grease.

17. A process according to claim 5 wherein the diisocyanate is selected from the group consisting of: diphenylmethane diisocyanate, phenylene diisocyanate, diphenyl diisocyanate, phenyl diisocyanate, naphthylene diisocyanate, tolylene orthodiisocyanate, tolylene diisocyanate, and a combination thereof.

18. A process according to claim 5 wherein the monoamine is selected from the group consisting of: octylamine, dodecylamine, tetradecylamine, hexadecylamine, octadecylamine, oleylamine, aniline, benzyl amine, p-toluidine, p-chloro-aniline, m-xylidine, and a combination thereof.

19. A process according to claim 5 wherein the diamine is selected from the group consisting of: ethylenediamine, propylenediamine, butylenediamine, pentylenediamine, hexamethylenediamine, polyoxymethylene diamine, polyoxyethylene diamine, polyoxypropylene diamine, polyoxyisopropylene diamine, polyetheramine, triethylene glycol diamine, and a combination thereof.

20. A process according to claim 5 wherein the alcohol is selected from the group consisting of: 1-dodecanol, 1-tetradecanol, 1-hexadecanol, 1-octadecanol, cis-9-octadecen-1-ol, 9-octadecadien-1-ol, 12-octadecadien-1-ol, and a combination thereof.

21. A process according to claim 5 wherein the first feed component further comprises a base oil.

22. A process according to claim 5 wherein the second feed component further comprises a base oil.

23. A process according to claim 5 wherein the third feed component further comprises a base oil.

\* \* \* \* \*